(12) United States Patent
Annoni et al.

(10) Patent No.: US 9,938,540 B2
(45) Date of Patent: Apr. 10, 2018

(54) GENE VECTOR FOR INDUCING TRANSGENE-SPECIFIC IMMUNE TOLERANCE

(75) Inventors: Andrea Annoni, Milan (IT); Alessio Cantore, Milan (IT); Luigi Naldini, Milan (IT); Maria Grazia Roncarolo, Milan (IT)

(73) Assignees: Ospedale San Raffaele S.r.l., Milan (IT); Fondazione Telethon, Rome (IT)

( * ) Notice: Subject to any disclaimer, the term of this patent is extended or adjusted under 35 U.S.C. 154(b) by 0 days.

(21) Appl. No.: 13/128,761

(22) PCT Filed: Nov. 11, 2009

(86) PCT No.: PCT/IB2009/007530
§ 371 (c)(1),
(2), (4) Date: May 11, 2011

(87) PCT Pub. No.: WO2010/055413
PCT Pub. Date: May 20, 2010

(65) Prior Publication Data
US 2011/0218234 A1    Sep. 8, 2011

Related U.S. Application Data

(60) Provisional application No. 61/113,616, filed on Nov. 12, 2008.

(51) Int. Cl.
| | |
|---|---|
| *A61K 39/00* | (2006.01) |
| *C07H 21/04* | (2006.01) |
| *C12N 5/10* | (2006.01) |
| *C12N 15/63* | (2006.01) |
| *C12N 15/86* | (2006.01) |
| *C12N 15/11* | (2006.01) |

(52) U.S. Cl.
CPC ............ *C12N 15/86* (2013.01); *C12N 15/111* (2013.01); *C12N 2310/141* (2013.01); *C12N 2320/00* (2013.01); *C12N 2740/16043* (2013.01); *C12N 2830/008* (2013.01); *C12N 2840/102* (2013.01)

(58) Field of Classification Search
CPC ................ C12N 15/111; C12N 15/86; C12N 2310/141; C12N 2740/16043; C12N 2830/008; C12N 2840/102
USPC .... 435/6, 91.1, 91.31, 455, 320.1, 6.1, 6.11, 435/91.3, 325; 514/44; 536/23.1, 23.2, 536/24.5; 424/9.1
See application file for complete search history.

(56) References Cited

U.S. PATENT DOCUMENTS

2003/0130221 A1    7/2003  High et al.
2009/0004668 A1*   1/2009  Chen et al. .................. 435/6

FOREIGN PATENT DOCUMENTS

| WO | WO2007/000668 | 1/2007 |
| WO | WO2007/071994 | 6/2007 |
| WO | WO2008/071959 | 6/2008 |

OTHER PUBLICATIONS

High et al., cited on IDS Jul. 11, 2011.*
Doench et al., Genes & Dev., vol. 18, No. 5, pp. 504-511 (2004).*
Opalinska et al., Nature Rev., vol. 1, pp. 503-514 (2002).*
Brown B D et al., Endogenous microRNA can be broadly exploited to regulat transgene expression according to tissue, lineage and differentiation state, Nature Biotechnology, Dec. 2007, vol. 25, No. 12, pp. 1457-1467.*
Akbarpour M et al., Liver-directed, insulin-based gene therapy protects NOD Mice from Diabetes, American Society of Gene and Cell Therapy, Salt Lake City, May 15-18, 2013 Abstract.*
Ye X et al., Complete and sustained phenotypic correction of hemophilia B in mice following hepatic gene transfer of a high-expressing human factor IX plasmid, J Thromb Haemost 2003, 1, pp. 103-111.*
Al-Dosari M S et al., Nonviral Gene Delivery: Principle, Limitations, and Recent Progress, AAPS J., 2009, vol. 11, No. 4, pp. 671-681.*
Agudo J et al., The miR-126-VEGFR2 axis controls the innate response to pathogen-associated nucleic acids, Nature Immunology, Jan. 2014, vol. 15, No. 1, pp. 54-62.*
Johanson T et al., A microRNA expression atlas of mouse dendritic cell development, Immunology and Cell Biology, 2014, pp. 1-6.*
Betel D et al., The microRNA.org resource: targets and expression, Nucleic Acids Research, 2008, vol. 36, D149-153.*
Chen C-Z et al., MicroRNAs modulate hematopoietic lineage differentiation, Science, 2004, vol. 303, pp. 83-86.*
Philippe, S., et al., "Lentiviral vectors with a defective integrase allow efficient and sustained transgene expression in vitro and in vivo," Proceedings of the National Academy of Sciences of USA, National Academy of Science, Washington, D.C., US, vol. 103, No. 47, Nov. 21, 2006, pp. 17684-17689.
Cerullo, V., et al., "Antigen-specific tolerance of human alpha(1)-antitrypsin induced by helper-dependent adenovirus," Human Gene Therapy, vol. 18, No. 12, Dec. 2007, pp. 1215-1224.
Annoni A. et al., 'In vivo delivery of a microRNA regulated transgene induces antigen-specific regulatory T cells and promotes immunological tolerance', Blood, Dec. 10, 2009;114(25):5152-61.
Barad, O., Meiri, E., Avniel, A., Aharonov, R., Barzilai, A., Bentwich, I., Einav, U., Gilad, S., Hurban, P., Karov, Y., et al. (2004). MicroRNA expression detected by oligonucleotide microarrays: system establishment and expression profiling in human tissues. Genome Res 14, 2486-2494.
Baskerville, S., and Bartel, D. P. (2005). Microarray profiling of microRNAs reveals frequent coexpression with neighboring miRNAs and host genes. Rna 11, 241-247.
Brennecke, J., Stark, A., Russell, R. B., and Cohen, S. M. (2005). Principles of microRNA-target recognition. PLoS Biol No. 3, e85 or pp. 0404-0418.
Brown BD et al., 'A microRNA-regulated lentiviral vector mediates stable correction of hemophilia B mice' Blood, vol. 110, 2007, p. 4144-4152.

(Continued)

*Primary Examiner* — Jane J Zara
(74) *Attorney, Agent, or Firm* — Steptoe & Johnson LLP

(57) ABSTRACT

A gene vector adapted for transient expression of a transgene in a peripheral organ cell comprising a regulatory sequence operably linked to a transgene wherein the regulatory sequence prevents or reduces expression of said transgene in hematopoietic lineage cells.

24 Claims, 3 Drawing Sheets

(56) References Cited

OTHER PUBLICATIONS

Brown BD, Venneri MA, Zingale A, Sergi Sergi L, Naldini L.(2006) Endogenous microRNA regulation suppresses transgene expression in hematopoietic lineages and enables stable gene transfer. Nat Med. May;12(5):585-91. Epub Apr. 23, 2006.

Brown, B. D., and Lillicrap, D. (2002). Dangerous liaisons: the role of "danger" signals in the immune response to gene therapy. Blood 100, 1133-1140.

Brown, B. D., Shi, C. X., Rawle, F. E., Tinlin, S., McKinven, A., Hough, C., Graham, F. L., and Lillicrap, D. (2004b). Factors influencing therapeutic efficacy and the host immune response to helper-dependent adenoviral gene therapy in hemophilia A mice. J Thromb Haemost 2, 111-118.

Calin, G. A., Liu, C. G., Sevignani, C., Ferracin, M., Felli, N., Dumitru, C. D., Shimizu, M., Cimmino, A., Zupo, S., Dono, M., et al. (2004a). MicroRNA profiling reveals distinct signatures in B cell chronic lymphocytic leukemias. Proc Natl Acad Sci U S A 101, 11755-11760.

Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004b). Human microRNA genes are frequently located at fragile sites and genomic regions involved in cancers. Proc Natl Acad Sci U S A 101, 2999-3004.

Cao O et al., Induction and role of regulatory CD4+CD25_T cells in tolerance to the transgene product following hepatic in vivo gene transfer, Blood, 15 Aug 2007, vol. 110, No. 4, p. 1132-1140.

Cao Ou et al., Emerging role of regulatory T cells in gene transfer, Current Gene Therapy, Oct. 1, 2007, vol. 7, No. 5, p. 381-390 XP009128732 ISSN 1566-5232 DOI: 10.2174/156652307782151506.

Chen, C. Z., and Lodish, H. F. (2005). MicroRNAs as regulators of mammalian hematopoiesis. Semin Immunol 17, 155-165.

Chen, C. Z., Li, L., Lodish, H. F., and Bartel, D. P. (2004). MicroRNAs modulate hematopoietic lineage differentiation. Science 303, 83-86.

De Geest, B. R., Van Linthout, S. A., and Collen, D. (2003). Humoral immune response in mice against a circulating antigen induced by adenoviral transfer is strictly dependent on expression in antigen-presenting cells. Blood 101, 2551-2556.

Follenzi, A., Battaglia, M., Lombardo, A., Annoni, A., Roncarolo, M. G., and Naldini, L. (2004). Targeting lentiviral vector expression to hepatocytes limits transgene-specific immune response and establishes long-term expression of human antihemophilic factor IX in mice. Blood 103, 3700-3709.

Follenzi, A., Sabatino, G., Lombardo, A., Boccaccio, C., and Naldini, L. (2002). Efficient gene delivery and targeted expression to hepatocytes in vivo by improved lentiviral vectors. Hum Gene Ther 13, 243-260.

Griffiths-Jones, S., Grocock, R. J., van Dongen, S., Bateman, A., and Enright, A. J. (2006). miRBase: microRNA sequences, targets and gene nomenclature. Nucleic Acids Res 34, D140-144.

He, L.; Hannon, G. J.: 'MicroRNAs: small RNAs with a big role in gene regulation' Nat Rev Genet vol. 5, 2004, pp. 522-531.

Houbaviy, H. B., Murray, M. F., and Sharp, P. A. (2003). Embryonic stem cell-specific MicroRNAs. Dev Cell 5, 351-358.

Iorio, M. V., Ferracin, M., Liu, C. G., Veronese, A., Spizzo, R., Sabbioni, S., Magri, E., Pedriali, M., Fabbri, M., Campiglio, M., et al. (2005). MicroRNA gene expression deregulation in human breast cancer. Cancer Res 65, 7065-7070.

Kasashima, K. et al., Altered expression profilesi of microRNAs during TPA-induced differentiation of HL-60 cells, Biochem Biophys Res Commun., 2004, vol. 322, No. 2, 2004, pp. 403-410.

Kasashima, K., Sakota, E., and Kozu, T. (2004). Discrimination of target by siRNA: designing of AML1-MTG8 fusion mRNA-specific siRNA sequences. Biochimie 86, 713-721.

Krichevsky AM et al, A microRNA array reveals extensive regulation of microRNAs during brain development, RNA (2003), 9:1274-1281.

Lagos-Quintana, M., Rauhut, R., Yalcin, A., Meyer, J., Lendeckel, W., and Tuschl, T. (2002). Identification of tissue-specific microRNAs from mouse. Curr Biol 12, 735-739.

Leavitt AD, Robles G, Alesandro N, Varmus HE. (1996) Human immunodeficiency virus type 1 integrase mutants retain in vitro integrase activity yet fail to integrate viral DNA efficiently during infection. J Virol. Feb;70(2):721-8.

Lombardo A, Genovese P, Beausejour CM, Colleoni S, Lee YL, Kim KA, Ando D, Urnov FD, Galli C, Gregory PD, Holmes MC, Naldini L. (2007) Gene editing in human stem cells using zinc finger nucleases and integrase-defective lentiviral vector delivery. Nat Biotechnol. 25(11):1298-306.

Lüth S, Huber S, Schramm C, Buch T, Zander S, Stadelmann C, Brück W, Wraith DC, Herkel J, Lohse AW. (2008) Ectopic expression of neural autoantigen in mouse liver suppresses experimental autoimmune neuroinflammation by inducing antigen-specific Tregs. J Clin Invest. 118(10):3403-3410.

Mansfield, J. H., Harfe, B. D., Nissen, R., Obenauer, J., Srineel, J., Chaudhuri, A., Farzan-Kashani, R., Zuker, M., Pasquinelli, A. E., Ruvkun, G., et al. (2004). MicroRNA-responsive 'sensor' transgenes uncover Hox-like and other developmentally regulated patterns of vertebrate microRNA expression. Nat Genet 36, 1079-1083.

Marodon G, Fisson S, Levacher B, Fabre M, Salomon BL, Klatzmann D. (2006) Induction of antigen-specific tolerance by intrathymic injection of lentiviral vectors. Blood. 108(9):2972-8.

Matrai J et al., Hepatocyte-targeted expression by integrase-defective lentiviral vectors induces antigen-specific tolerance in mice with low genotoxic risk, Hepatology. May 2011;53(5):1696-1707. doi: 10.1002/hep.24230.

Metzler M et al, High expression of precursor microRNA-155/BIC RNA in children with Burkitt lymphoma, Genes Chromosomes Cancer (2004) 39:167-169.

Michael M et al, Reduced accumulation of specific microRNAs in colorectal neoplasia, Mol Can Res (2003) 1:882-891.

Mingozzi, F., Liu, Y. L., Dobrzynski, E., Kaufhold, A., Liu, J. H., Wang, Y., Arruda, V. R., High, K. A., and Herzog, R. W. (2003). Induction of immune tolerance to coagulation factor IX antigen by in vivo hepatic gene transfer. J Clin Invest 111, 1347-1356.

Naldini L et al., In vivo gene delivery and stable transduction of nondividing cells by a lentiviral vector, Science, Apr. 12, 1996;272(5259):263-7.

Naldini L, Blomer U, Gage FH, Trono D, Verma IM. (1996) Efficient transfer, integration, and sustained long-term expression of the transgene in adult rat brains injected with a lentiviral vector. Proc Natl Acad Sci U S A. 93(21):11382-8.

Nightingale SJ, Hollis RP, Pepper KA, Petersen D, Yu Xj, Yang C, Bahner I, Kohn DB. (2006) Transient gene expression by nonintegrating lentiviral vectors. Mol Ther. Jun;13(6):1121-32. Epub Mar. 23, 2006.

Ping Jin et al., Differentiation of two types of mobilized peripheral blood stem cells by microRNA and cDNA expression analysis, Journal of Translational Medicine, 2008, vol. 6, No. 39.

Schiano TD et al., Management of HCV Infection and Liver Transplantation, Int J Med Sci, 2006, vol. 3, p. 79-83.

Sempere, L. F., Freemantle, S., Pitha-Rowe, I., Moss, E., Dmitrovsky, E., and Ambros, V. (2004). Expression profiling of mammalian microRNAs uncovers a subset of brain-expressed microRNAs with possible roles in murine and human neuronal differentiation. Genome Biol 5, R13.

Thomas, C. E., Ehrhardt, A., and Kay, M. A. (2003), Progress and problems with the use of viral vectors for gene therapy, Nat Rev Genet 4, 346-358.

Vargas J Jr, Gusella GL, Najfeld V, Klotman ME, Cara A. (2004) Novel integrase-defective lentiviral episomal vectors for gene transfer. Hum Gene Ther. 15(4):361-72.

Verma, I. M., and Weitzman, M. D. (2005). Grnr Therapy: Twenty-First Century Medicine. Annu Rev Biochem 74, 711-738.

Yáñez-Muñoz RJ, Balaggan KS, MacNeil A, Howe SJ, Schmidt M, Smith AJ, Buch P, MacLaren RE, Anderson PN, Barker SE, Duran Y, Bartholomae C, von Kalle C, Heckenlively JR, Kinnon C, Ali

(56) References Cited

OTHER PUBLICATIONS

RR, Thrasher AJ. (2006) Effective gene therapy with nonintegrating lentiviral vectors. Nat Med. 12(3):348-53.

* cited by examiner

GENE VECTOR FOR INDUCING TRANSGENE-SPECIFIC IMMUNE TOLERANCE

CLAIM FOR PRIORITY

This application claims priority under 35 USC 371 to International Application No. PCT/IB2009/007530, filed on Nov. 11, 2009, which claims priority to U.S. Provisional Application No. 61/113,616, filed on Nov. 12, 2008, each of which is hereby incorporated by reference in its entirety.

FIELD OF THE INVENTION

The present invention relates to gene vectors for use in gene transfer and therapy applications, and to methods of producing them, and uses thereof.

BACKGROUND TO THE INVENTION

Some viral vectors have been shown to effectively induce immunity to a transgene product. This property is being exploited to develop novel vaccines based on gene transfer of autologous antigens, such as tumor-associated antigens, or exogenous antigens, such as those from infectious agents.

Among these vectors, adenoviral vectors, adeno-associated viral vectors and lentiviral vectors (LVs) have all been shown to give rise to transgene-directed immunity under specific conditions, in some case even being able to break pre-existing tolerance.

However, the induction of an immune response may neutralize a therapeutic protein replacing a defect protein. The unwanted immune response against antigens is also a limiting factor in conventional protein therapy (such as protein replacement therapy).

Whether the type of immune response induced by these approaches can be modulated by vector design and route of administration has long been questioned. Use of promoter targeting expression to specific cell types, such as hepatocytes, has been shown to alleviate the immune response, although it was insufficient to fully prevent its development in challenging settings.

The problem has been addressed in a number of attempts to induce immune tolerance against antigen. For example, injection into the thymus with a lentiviral vector expressing the hemagglutinin antigen (HA) in TCR-HA transgenic mice resulted in the induction of antigen-specific tolerance in the thymus and in the peripheral system (Marodon et al, 2006). Induction of immune tolerance against a specific antigen by sustained adeno-associated viral gene expression in the liver has been described for coagulation factor IX (hF.IX) (Mingozzi et al., 2003). It was also reported that expression of the neural autoantigen myelin basic protein (MBP) in the liver induced protection from autoimmune neuroinflammation in a mouse model of multiple sclerosis (Lüth et al, 2008).

We recently demonstrated that miRNA-based regulation can improve the stringency of transgene expression of LV administered to mice, is able to suppress induction of immunity against intracellular and secreted transgene products and can induce active tolerance to it. WO2007000668 describes that by using miRNA regulation to de-target transgene expression of clotting factor IX from hematopoietic lineages in hemophilia B mice it was possible to prevent immune-mediated vector clearance and enable stable gene transfer. Whereas this discovery has tremendous potential for the development of gene therapy applications as it allows for long-lasting stable expression of a therapeutic gene product delivered by a vector, the immunological outcome of tolerance induction was associated with and conceivably dependent on the stable long-term maintenance of the vector genome within the target cells, as achieved by vector integration in the case of LV. The potential dependence of the tolerogenic outcome of miRNA-regulated LV delivery from high-level vector integration and long-term robust expression within hepatocytes may significantly limit the potential applications of the discovery outside of gene replacement approaches for the correction of disease.

In particular, the efficient integration of LV within target hepatocytes may raise significant safety concerns associated with the risk of insertional mutagenesis and the triggering of oncogenesis.

Thus, the development of novel strategies that could exploit the type of antigen presentation made possible by miRNA-regulated LV without depending on or giving rise to stable long term genetic modification of recipient cells would represent a significant advancement in gene therapy.

The present invention addresses these needs and demonstrates the induction of transgene-specific active immune tolerance without the need for high level of transgene expression and vector insertion into the target cell genome.

STATEMENTS OF THE INVENTION

The inventors demonstrate that transient transgene expression, which only reaches low levels and is short-lived, leads to a robust state of immunological tolerance if the expression is initiated by a gene delivery approach using non-integrating vectors, and de-targeted from hematopoetic lineage cell.

According to one aspect of the present invention there is provided a gene vector for transient expression of a transgene in a peripheral organ cell comprising a regulatory sequence operably linked to a transgene wherein the regulatory sequence prevents or reduces expression of said transgene in hematopoietic lineage cells.

According to another aspect of the present invention there is provided an integration defective lentiviral vector comprising a transgene wherein the vector comprises a regulatory sequence operably linked to the transgene wherein the regulatory sequence prevents or reduces expression of said transgene in hematopoietic lineage cells. Preferably the transgene is expressed in a peripheral organ.

The term "transient expression" describes expression of a transgene wherein the expression is not stable over a prolonged length of time. Preferably, the transgene does not integrate into the host genome. More specifically, transient expression is expression which is substantially lost within 12 weeks following introduction of the vector into the cell. Preferably, expression is substantially lost within 6, 4 or 2 weeks following introduction of the vector into the cell.

Preferably, expression levels are reduced to less than 30, 20, 10, 5, 2, 1, 0.5 or 0.1% of the initial expression levels within 12 weeks following introduction of the vector into the cell.

Preferably, after 12 weeks following introduction of the vector into the cell, expression levels are reduced to less than 30, 20, 10, 5, 2, 1, 0.5 or 0.1% of the maximum expression levels observed during this period.

In one embodiment, expression levels are reduced to less than 30, 20, 10, 5, 2, 1, 0.5 or 0.1% of the initial expression levels within 6 weeks following introduction of the vector into the cell.

In one embodiment, after 6 weeks following introduction of the vector into the cell, expression levels are reduced to less than 30, 20, 10, 5, 2, 1, 0.5 or 0.1% of the maximum expression levels observed during this period.

In another embodiment, expression levels are reduced to less than 30, 20, 10, 5, 2, 1, 0.5 or 0.1% of the initial expression levels within 4 weeks following introduction of the vector into the cell.

In one embodiment, after 4 weeks following introduction of the vector into the cell, expression levels are reduced to less than 30, 20, 10, 5, 2, 1, 0.5 or 0.1% of the maximum expression levels observed during this period.

In another embodiment, expression levels are reduced to less than 30, 20, 10, 5, 2, 1, 0.5 or 0.1% of the initial expression levels within 2 weeks following introduction of the vector into the cell.

In one embodiment, after 2 weeks following introduction of the vector into the cell, expression levels are reduced to less than 30, 20, 10, 5, 2, 1, 0.5 or 0.1% of the maximum expression levels observed during this period.

The expression can be controlled at the transcriptional level or at the translational level.

The regulatory sequence can comprise elements which prevent or reduce the expression of the encoded transgene. Such elements could be recognition sequences which bind or interact with modulators. The modulators could be endogenous modulators present in the cell. Alternatively, the modulators could be exogeneous molecules which are introduced into the cell. Preferably, the modulators are microRNAs.

The term "operably linked" means that the components described are in a relationship permitting them to function in their intended manner.

In one embodiment, the gene vector is a viral gene vector which transiently expresses the transgene.

In another embodiment the gene vector may be in the form of a non-viral gene transfer vector which transiently expresses the transgene. For example, the gene transfer vector may comprise, or be in the form of, an expression vector or plasmid which comprises the regulatory sequence and a transgene. Alternatively, the vector may be in the form of naked DNA.

Non-viral delivery systems include but are not limited to DNA and RNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

Viral vectors for use in the invention include but are not limited to integration defective retroviral vectors, integration defective lentiviral vectors (IDLV), integration defective spuma/foamy vectors, herpes viral vectors, baculoviral and SV-40-based vectors, and hybrid vectors made by a combination of non-viral and/or viral components derived from the above mentioned or other types of viral vectors.

In a particularly preferred embodiment the vector is an integration defective lentiviral vector (IDLV vector). Preferably, the IDLV vector is derived from HIV.

Preferably the regulatory sequence comprises one or more target sequences for an miRNA sequence(s).

Preferably the target sequence is the target of an miRNA selected from the group of miR-142, miR-155 and miR-223.

In one embodiment the regulatory sequence comprises a combination of target sequence for the same or different miRNAs selected from the group consisting of miR-142, miR-155 and miR-223. More than one copy of an miRNA target sequence included in the vector may increase the effectiveness of the system. Also it is envisaged that different miRNA target sequences could be included. For example, vectors which express more than one transgene may have the transgene under control of more than one miRNA target sequence, which may or may not be different. The miRNA target sequences may be in tandem, but other arrangements are envisaged. The transgene expression cassette, containing miRNA target sequences, may also be inserted within the vector in antisense orientation. Antisense orientation may be useful in the production of viral particles to avoid expression of gene products which may otherwise be toxic to the producer cells. Preferably, the vector comprises 1, 2, 3, 4, 5, 6, 7 or 8 copies of the same or different miRNA target sequence. In one preferred embodiment, the vector comprises 4 copies of miR-142 target sequences.

In one embodiment the target sequence is fully or partially complementary to the miRNA. The term "fully complementary" means that the target sequence has a nucleic acid sequence which is 100% complementary to the sequence of the miRNA which recognises it. The term "partially complementary" means that the target sequence is only in part complementary to the sequence of the miRNA which recognises it, whereby the partially complementary sequence is still recognised by the miRNA. In other words, a partially complementary target sequence in the context of the present invention is effective in recognising the corresponding miRNA and effecting prevention or reduction of transgene expression in cells expressing that miRNA.

In one embodiment, the transgene encodes a therapeutic protein. Preferably the transgene encodes a tumour suppressor protein, an enzyme, a pro-drug activating enzyme, an immunomodulatory molecule, an antibodies, an engineered immunoglobulin-like molecule, a fusion protein, a hormone, a membrane protein, a vasoactive protein, a peptide, a cytokine, a chemokine, an anti-viral protein, an antisense RNA or a ribozyme.

In one embodiment the transgene product is an antigen. Preferably, the antigen is selected from the group of endogenous antigens, exogenous antigens, alloantigens and autoantigens. Furthermore, the transgene product may contain one or more antigens.

In one embodiment the antigen is an allergen.

More preferably, the antigen is an exogenous antigen.

In one embodiment the transgene is operably linked to a tissue specific promoter.

In a preferred embodiment the tissue specific promoter is a promoter specific for a cell in a peripheral organ. Preferably, the peripheral organ is selected from the group consisting of liver, muscle, thymus, spleen and lymphnodes.

Preferably the peripheral organ is the liver.

In another preferred embodiment the tissue specific promoter is a hepato-specific promoter.

In a further preferred embodiment the tissue specific promoter is a promoter selected from the group of albumin promoter, trans-thyretin promoter, alpha1-antitrypsin promoter, synthetic apoE/alpha1-antitrypsin promoter and synthetic ET promoter.

In one embodiment the vector is in the form of a viral vector particle. The term "viral particle" refers to the packaged retroviral vector that is preferably capable of binding to and entering target cells. The components of the particle may be modified with respect to the wild type virus. For example, the Env proteins in the proteinaceous coat of the particle may be genetically modified in order to alter their targeting specificity or achieve some other desired function. Preferably, the viral vector preferentially transduces a certain cell type or cell types.

The integration defective retroviral vector, such as the IDLV, can be produced, for example, either by packaging the vector with catalytically inactive integrase (such as an HIV integrase bearing the D64V mutation in the catalytic site; Naldini et al., Science 1996, and PNAS USA 1996, Leavitt et al. J Virol. 1996) or by modifying or deleting essential att sequences from the vector LTR (Nigthingale et al. Mol Ther 2006), or by a combination of the above.

According to another aspect of the present invention there is provided a set of DNA constructs for producing a viral vector particle of the present invention comprising a packagable lentiviral vector genome, gag, pol and env or functional substitutes thereof.

In one embodiment, the set of DNA constructs encode a defective integrase.

In another embodiment the set of DNA constructs comprise altered LTR sites so as to prevent integration.

In another embodiment the set of DNA constructs encode a defective integrase and comprise altered LTR sites to prevent integration.

According to another aspect of the present invention there is provided a process for preparing a viral vector particle comprising introducing the DNA constructs according to the present invention into a host cell, and obtaining the viral vector particle.

According to another aspect of the present invention there is provided a viral vector particle produced by the process of the present invention.

According to another aspect of the present invention there is provided a pharmaceutical composition comprising the vector or particle according to the present invention together with a pharmaceutically acceptable diluent, excipient or carrier.

According to another aspect of the present invention there is provided a cell infected or transduced with the vector or particle according to the present invention. For example, the cell may comprise the corresponding miRNA. The cell may be transduced or infected in an in vivo or in vitro scenario. The cell may be derived from or form part of an animal, preferably a mammal, such as a human or mouse.

According to another aspect of the present invention there is provided the vector of the present invention for inducing or enhancing immunological tolerance against an antigen in a subject. The antigen could be endogenously expressed as part of a gene therapy or exogenously administered.

According to another aspect of the present invention there is provided the vector of the present invention wherein the antigen is an exogenous antigen administered as part of a protein replacement therapy. Protein replacement therapy is a therapeutic approach useful in the treatment of protein deficiencies, storage disorders, metabolic deficiencies and hormonal replacement therapies. Examples of protein deficiencies include clotting factor deficiencies such as hemophilias. Examples of storage disease include: Lysosomal storage disorders (Gaucher's disease, Niemann Pick disease, Mucopolysaccharidoses), Disorders of carbohydrate metabolism (glycogen storage disease), Disorders of amino acid metabolism (phenylketonuria, maple syrup urine disease), glutaric acidemia type 1, Disorders of organic acid metabolism (organic acidurias) (alcaptonuria), Disorders of fatty acid oxidation and mitochondrial metabolism (medium chain acyl dehydrogenase deficiency (glutaric acidemia type 2), Disorders of porphyrin metabolism (acute intermittent porphyria), Disorders of purine or pyrimidine metabolism (Lesch-Nyhan syndrome), Disorders of steroid metabolism (congenital adrenal hyperplasia), Disorders of mitochondrial function (Kearns-Sayre syndrome), Disorders of peroxisomal function (Zellweger syndrome).

According to another aspect of the present invention there is provided the vector of the present invention for treating or preventing a disease selected from the group of autoimmune diseases, allergic diseases, immune-mediated diseases and graft vs. host disease. Examples of autoimmune diseases include: Acute disseminated encephalomyelitis (ADEM), Addison's disease, Ankylosing spondylitis, Antiphospholipid antibody syndrome (APS), Autoimmune hemolytic anemia, Autoimmune hepatitis, Autoimmune inner ear disease, Bullous pemphigoid, Coeliac disease, Chagas disease, Chronic obstructive pulmonary disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Idiopathic thrombocytopenic purpura, Interstitial cystitis, Lupus erythematosus, Morphea, Multiple sclerosis, Myasthenia gravis, Narcolepsy, Neuromyotonia, Pemphigus Vulgaris, Pernicious anaemia, Polymyositis, Primary biliary cirrhosis, Rheumatoid arthritis, Schizophrenia, Scleroderma, Sjögren's syndrome, Temporal arteritis (also known as "giant cell arteritis"), Vasculitis, Vitiligo, Wegener's granulomatosis.

Autoimmune is any disease caused by adaptive immunity that becomes misdirected at healthy cells and/or tissues of the body. Autoimmune diseases are characterized by T and B lymphocytes that aberrantly target self-proteins causing injury and or malfunction of an organ, tissue, or cell-type within the body (for example, pancreas, brain, thyroid or gastrointestinal tract) to cause the clinical manifestations of the disease.

In one embodiment the transgene encodes a self protein or a fragment or peptide derived from it. The vector of the present invention can be used to induce tolerance to the self protein. The invention is particularly related to the vectors and methods for treating or preventing autoimmune diseases associated with one or more self-protein (s) such as in multiple sclerosis, rheumatoid arthritis, insulin dependent diabetes mellitus, autoimmune uveitis, primary biliary cirrhosis, myasthenia gravis, Sjogren's syndrome, pemphigus vulgaris, scleroderma, pernicious anemia, systemic lupus erythematosus (SLE) and Grave's disease.

Several examples of autoimmune diseases and the associated self-protein are set forth below. The vector of the present invention may encode one or more of these self-proteins or a fragment or peptide derived from them. The vector can be used to induce tolerance to the self protein.

Multiple sclerosis: myelin basic protein, proteolipid protein, myelin system associated glycoprotein, cyclic nucleotide phosphodiesterase, myelin-associated glycoprotein, myelin-associated oligodendrocytic basic protein, myelin oligodendrocyte glycoprotein, alpha-B-crystalline Guillian Barre Syndrome: peripheral myelin protein I Insulin Dependent Diabetes Mellitus: tyrosine phosphatase IA2, IA-2; glutamic acid decarboxylase (65 and 67 kDa forms), carboxypeptidase H, insulin, proinsulin, preproinsulin, heat shock proteins, glima 38, islet cell antigen 69 KDa, p52, islet cell glucose transporter GLUT-2

Rheumatoid Arthritis: Immunoglobulin, fibrin, filaggrin, type 1, II, III, IV, V, IX, and X1 collagens, GP-39, hnRNPs Autoimmune Uveitis: S-antigen, interphotoreceptor retinoid binding protein (IRBP), rhodopsin, recoverin Primary Biliary Cirrhosis: pyruvate dehydrogenase complexes (2-oxoacid dehydrogenase)

Autoimmune Hepatitis: Hepatocyte antigens, cytochrome P450

Pemphigus vulgaris: Desmoglein-1,-3

Myasthenia Gravis: acetylcholine receptor

Autoimmune gastritis: H+/K+ ATPase, intrinsic factor

Pernicious Anemia: intrinsic factor

Polymyositis: histidyl tRNA synthetase, other synthetases, other nuclear antigens Autoimmune Thyroiditis: Thyroglobulin, thyroid peroxidase Graves's Disease: Thyroid-stimulating hormone receptor Vitiligo: Tyrosinase, tyrosinase-related protein-2

Systemic Lupus Eryth.: nuclear antigens: DNA, histones, ribonucleoproteins

Celiac Disease: Transglutaminase

In a preferred embodiment, the autoimmune disease is insulin dependent diabetes mellitus. In this embodiment, the transgene may encode a protein or a peptide derived from that protein, selected from the group consisting of insulin, insulin β chain, preproinsulin, proinsulin, glutamic acid decarboxylase 65 kDa and 67 kDa forms, tyrosine phosphatase IA2 or IA-2b, carboxypeptidase H, heat shock proteins, glima 38, islet cell antigen 69 kDa, p52, and islet cell glucose transporter (GLUT 2). Preferably the peptides are derived from the insulin β chain and display epitopes of MHC class I and II for induction of tolerance in diabetes. In one embodiment the transgene is insulin β chain 9-23 peptide In one embodiment the autoimmune disease is rheumatoid arthritis. In this embodiment, the transgene may encode a protein or a peptide derived from that protein selected from the group consisting of type 11 collagen; hnRNP A2/RA33; Sa; filaggrin; keratin; cartilage proteins including gp39; collagens type 1, III, IV, V, IX, XI; HSP-65/60; RNA polymerase; hnRNP-B1; hnRNP-D; and aldolase A.

In another embodiment, the autoimmune disease is primary biliary cirrhosis. In this embodiment, the transgene may encode a protein or a peptide derived from that protein selected from the group consisting of pyruvate dehydrogenase complex (PDC), E2 74 kDa subunit of PDC, protein X of PDC (E-3Binding protein), 2-oxoacid dehydrogenase complex (OADC), 2-oxoglutarate dehydrogenase complex (OGDC), branched-chain 2 OADC, and PBC lipoyl domain.

In another embodiment the vector of the present invention may be used for induction of tolerance to a viral antigen such as in the context of organ transplantation in patients infected with hepatitis C virus (HCV). Thus, the transgene may encode a viral antigen, preferably an HCV antigen.

According to another aspect of the present invention there is provided the vector of the present invention for inducing antigen-specific CD4+ CD25+ FOXP3+ regulatory T cells for the delivered transgene product Some Further Key Advantages of the Invention The vectors according to the present invention are particularly useful in a strategy for inducing immune tolerance by de-targeting transgene expression from specific cell types upon a gene delivery approach.

The inventors demonstrate that transient transgene expression, which only reaches low levels and is short-lived, leads to a robust state of immunological tolerance if the expression is initiated by gene delivery and de-targeted from hematopoetic lineage cell. In particular, IDLV-mediated expression of the transgene is transient in the liver and most of the vector itself is lost after a few weeks. However, the transgene expression is surprisingly sufficient to induce immunological tolerance to the antigen encoded by transgene, which is maintained after the transgene expression is lost in the target tissue.

The ability to exploit transient transgene expression combined with de-targeting of the transgene expression to induce immunological tolerance to a gene-encoded antigen has major therapeutic implications.

Current vector transcription control approaches mostly rely on the delivery of enhancer-promoter elements taken from endogenous genes (Thomas et al., 2003; Verma and Weitzman, 2005). Using these approaches, reconstitution of highly specific gene expression patterns, as often required for gene transfer and therapy applications, is limited by the delivery system, the vector capacity, and the positional effects of insertion (for integrating vectors). By developing new vectors which are only transiently expressed and which take advantage of endogenously expressed miRNAs for their regulation, the inventors have added a layer of control to the vectors that did not previously exist. This new approach allows specific repression of gene expression in selected cell types and lineages.

With this system we can reach much more stringent control of transgene expression than is currently possible with existing technologies.

The use of lentivirus-derived vectors is limited in clinical practice by the associated risk of insertional mutagenesis. In the present invention this risk has been overcome by using integration defective lentiviral vectors (IDLV). Preferably the vector is an integrase defective lentiviral vector.

The inventors demonstrate that IDLV mediated transgene expression reached only low levels and was short term. Furthermore within a short time following injection the transgene expression was almost completed lost in IDLV treated mice while it remained stable in those injected with LV. The transient presence and progressive loss over time make these vectors particularly useful in gene therapy application where the integration, stable presence or continuous expression is not desired.

The vectors of the present invention are particularly useful in the context of inducing immune tolerance. Genetic diseases can potentially be cured by the introduction of a functional copy of the defective gene (for example, through gene delivery of a transgene). Stable gene transfer results in the expression of the transgene and the supply of the functional transgene product. However, gene replacement therapy is complicated by the risk of an immune response against the therapeutic transgene product.

As a proof of this principle, the inventors demonstrated that IDLV encoding a miR-142-regulated transgene mediated a long-lasting and robust state of immunological tolerance, which cannot be broken by re-challenge with the antigen. The data below show that GFP transiently expressed by IDLV in the liver results in active tolerance.

A further usage of the invention is in the design of a vector system that expresses two transgenes with distinct expression profiles. Uses of this vector design include situations where a heterogeneous population of cells will be transduced, and expression of gene 1 is required in one of the cell types present, and expression of gene 2 is required in another cell type. This design could be used for therapeutic applications requiring both negative and positive selection of particular cells.

The miRNA-mediated approach for restricting gene expression has several advantages over other strategies of regulating transgenes. To date, most efforts to limit expression from professional antigen presenting cells (APCs) rely on tissue-specific promoters (Brown et al., 2004b; Follenzi et al., 2004; Mingozzi et al., 2003). Although this approach can successfully limit expression to target cells, 'leaky' expression in a fraction of non-target cells is observed. This occurs because the reconstituted promoter, modified for inclusion into a vector system, often loses some of its cell specificity and also because vector integration near active promoters and enhancers can activate the tissue-specific promoter and drive transgene expression. Because miRNA-mediated silencing occurs at the post-transcriptional level, promoter and enhancer trapping is irrelevant. As such, miRNA-regulation can be used to effectively de-target transgene expression from a particular cell type, while still allowing for broad tissue expression, as we have described here. miRNA regulation may also be used as a complimentary approach to regulating a transgene by promoter/enhancers. By including the miRNA target sequence in expression cassettes already under the control of a tissue-specific promoter, we add an additional layer of regulation which will eliminate off-target expression.

The vectors according to the present invention are particularly useful for systemic gene therapy in which the host immune response against the transgene limits therapeutic efficacy (Brown and Lillicrap, 2002). Studies from our laboratory and others indicate that a major factor contributing to the induction of a transgene-specific immune response following gene transfer is related to the site of transgene expression (Brown et al., 2004b; Follenzi et al., 2004). Vectors that are expressed in APCs of the hematopoietic system, such as macrophages and dendritic cells, are known to effectively trigger anti-transgene immune responses (De Geest et al., 2003).

Indeed, systemic administration of lentiviral vector, expressing a transgene under the control of the CMV promoter, led to a high incidence of transgene expression in APCs of the liver and spleen, and this resulted in immune-mediated clearance of cells expressing the transgene (Follenzi et al., 2004). In contrast, when the CMV promoter was substituted with the liver-specific albumin promoter there was a reduction in the frequency and strength of the immune response. Although the incidence of immunity was reduced by the use of the albumin promoter, some level of immune responses were still observed. This was likely due to low level transgene expression in APCs from the albumin promoter, a result of leaky transcriptional activity and promoter/enhancer trapping. Thus, the problem of transgene expression in non-target cells, which is caused by events occurring at the level of transcriptional regulation, is here overcome by utilizing the miRNA system of gene regulation that acts post-transcriptionally.

Thus, miRNA regulation, which de-targets rather than targets gene expression and functions at the post-transcriptional level, provides a unique means for overcoming the limitations of current gene delivery systems. By preventing transgene expression in hematopoietic lineages, while permitting high levels of expression in non-hematopoietic cells, miRNA regulation enables transgene expression in the absence of an immune response.

Upon vector administration in vivo, the present invention will avoid vector expression in antigen presenting cells of the immune system, which are part of the hematopoietic system, and thereby prevent the initiation of an immune response against the transgene. When applied to a tissue-specific promoter which targets expression in peripheral organ cells such as hepatocytes, it allows suppressing ectopic expression in a transduced APC. This solves a major hurdle and long-standing problem in gene transfer; namely, immune-mediated rejection of the transferred gene.

The ability to exploit vectors adapted for transient expression such as IDLY and, for example, miR-142 regulation to induce immunological tolerance to a gene-encoded antigen has major therapeutic implications. IDLY and, for example, miR-142 regulation is particularly useful to induce tolerance to exogenously administered antigens, such as in enzyme replacement and other types of protein-based therapies (i.e. in protein deficiencies, clotting disorders, storage disorders, metabolic deficiencies and hormonal replacement), to enhance tolerance to auto-antigens in individuals at risk of developing autoimmunity (such as in patients developing insulin-dependent diabetes), and may be useful to revert immunity/autoimmunity against exogenous or endogenous antigens in immune-mediated or allergic diseases (such as bowel inflammatory diseases, gluten enteropathy, insulin-dependent diabete). Furthermore, our approach to promote tolerance to one major auto- or allo-antigen may be able to suppress the immune response to other antigens in a cell, tissue and organ, thus improving graft survival in transplantation strategies.

In addition, the strategy described here may also be applicable to other gene delivery vehicles which only induce transient gene expression and which can be regulated by hematopoietic-specific miRNA, including viral, plasmid- and RNA-based delivery.

Further particular and preferred aspects of the present invention are set out in the accompanying independent and dependent claims. Features of the dependent claims may be combined with features of the independent claims as appropriate, and in combinations other than those explicitly set out in the claims.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

The present invention will be described further, by way of example only, with reference to preferred embodiments thereof as illustrated in the accompanying drawings, in which.

Figure 1A:
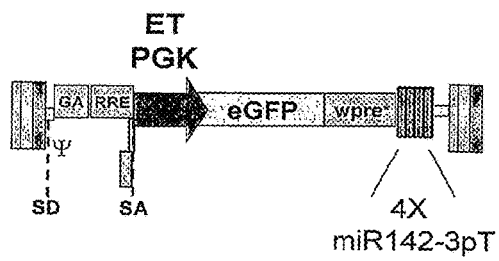
FIGS. 1A-1C. Evaluation of transgene expression and vector content after intravenous IDLV injection in mice.

(A) Schematic representation of the third-generation self-inactivating LV/IDLV used for these studies. SD: splicing donor site. SA: splicing acceptor site. ψ: packaging signal (including 5' portion of GAG gene (GA). RRE: Rev responsive element. cPPT: central polypurine tract. Wpre*: mutated woodchuck hepatitis virus post-regulatory elements. 142T: miR-142 target sequence made of 4 tandem copies of a sequence perfectly complementary to miR-142. (B) Representative image of liver sections obtained from mice injected with LV or IDLY and euthanized at 1 or 6 weeks after injection. Sections nuclei were stained with TOPRO-3. (C) Morphometric analysis of GFP$^+$ hepatocytes in immuno-stained sections and vector content in mice injected with 20 or 40 µg of p24 of LV (black) or IDLY (grey) and euthanized at 1, 3, 6 or 8 weeks after injection. Each bar represents an individual mice. The result is expressed as mean±SEM of GFP$^+$ hepatocytes in 5 different fields of 6-8 non-consecutive liver sections per mice. Circles show VCN (vector copy number) quantification. Each circle represents an individual mice.

FIG. 2. Primary and secondary immune responses to the vector encoded antigen.

Balb-c mice were injected intravenously with ID-PGK control, and with ID-PGK.142T or, alternatively, with ID-ET.142T and euthanized after 1, 3, and 8 weeks. (A) Proliferation rate of liver derived CD8$^+$ T cells was determined by Ki-67 staining. Effector CD8$^+$ T cells were sorted from central memory and naïve by CD62L expression. (B) CD8$^+$ T cells liver infiltration was evaluated by FACS analysis of MNC isolated from the liver. Data are expressed as the mean percentage±SD (n=3/group). Note that CD8$^+$ T cells liver infiltration in ID-ET.142T-treated mice resulted strongly reduced at the third week compared to ID-PGK-treated mice, suggesting that of CD8$^+$ T cells was efficiently expanded only in the absence of miR-142T regulation of Ag expression. (C) Transgene-specific primary immune response was evaluated in spleen and liver. The frequency of IFN-γ producing, GFP-specific CD8$^+$ T cells in the spleen was determined by ELISPOT 8 weeks post IDLY administration. Data are expressed as the mean±SD (liver n=3/group; spleen n=6/group) number of GFP-specific CD8$^+$ T cells per $10^6$ total CD8$^+$ T cells.

The ability to mount a secondary immune response to the vector-encoded Ag was studied in ID-PGK and ID-PGK.142T and/or ID-ET.142T treated mice re-exposing them to the Ag by DNA-vaccination. (D) Quantification of the absolute number of GFP-specific CD8$^+$ T cells infiltrating the liver 8 weeks post ID-LV injection. Note that Ag-specific CD8$^+$ T cells were expanded by DNA-vaccination only in mice receiving the ID-PGK control vector. Single values are plotted and mean±SD is shown (ID-PGK n=9/group; ID-PGK.142T n=6/group; ID-ET.142T n=3/group). VCN quantification is reported as mean±SD.

MICRORNAS (MIRNAS)

miRNAs are small, RNA molecules encoded in the genomes of plants and animals. These highly conserved, ~21-mer RNAs regulate the expression of genes by binding to specific mRNAs (He and Hannon, 2004).

miRNAs are a family of small, non-coding RNAs that regulate gene expression in a sequence-specific manner.

In summary from microRNAs: SMALL RNAS WITH A BIG ROLE IN GENE REGULATION, Lin He & Gregory J. Hannon *Nature Reviews Genetics* 5, 522-531 (2004):

MicroRNAs (miRNAs) are a family of ~21-25-nucleotide small RNAs that negatively regulate gene expression at the post-transcriptional level.

The founding members of the miRNA family, lin-4 and let-7, were identified through genetic screens for defects in the temporal regulation of *Caenorhabditis elegans* larval development.

Owing to genome-wide cloning efforts, hundreds of miRNAs have now been identified in almost all metazoans, including flies, plants and mammals.

MiRNAs exhibit temporally and spatially regulated expression patterns during diverse developmental and physiological processes.

The majority of the animal miRNAs that have been characterized so far affect protein synthesis from their target mRNAs. On the other hand, most of the plant miRNAs studied so far direct the cleavage of their targets.

The degree of complementarity between a miRNA and its target, at least in part, determines the regulatory mechanism.

In animals, primary transcripts of miRNAs are processed sequentially by two RNase-III enzymes, Drosha and Dicer, into a small, imperfect dsRNA duplex (miRNA: miRNA*) that contains both the mature miRNA strand and its complementary strand (miRNA*). Relative instability at the 5' end of the mature miRNA leads to the asymmetric assembly of the mature miRNA into the effector complex, the RNA-induced silencing complex (RISC).

Ago proteins are a key component of the RISC. Multiple Ago homologues in various metazoan genomes indicate the existence of multiple RISCs that carry out related but specific biological functions.

Bioinformatic prediction of miRNA targets has provided an important tool to explore the functions of miRNAs.

Several hundred miRNAs have been cloned and sequenced from mouse, human, *Drosphila, C, elegans* and *Arabidopsis*. Examples of such sequences may be found on www.sanger.ac.uk (Griffiths-Jones et al., 2006). Further miRNA target sequences may be searched at www.miRNA.org.

Like mRNAs, miRNA expression profiles appear to vary from tissue to tissue but are similar for identical tissues in different individuals (Baskerville and Bartel, 2005). Determining an miRNA with the desired expression profile may be achieved using techniques known to those skilled in the art. Once, the miRNA has been identified the corresponding target sequence can readily be determined using, for example, the databases indicated above.

For example, the mirVana™ miTNA Probe Set and mirVana™ miTNA Labelling Kit available from Ambion, Inc. may be used to compare the miRNA expression profiles in human tissues according to the manufacturer's instructions.

Another common way of identifying tissue-specific miRNAs is using Northern Blot. An example of such a technique is described in Lagos-Quintana M et al, Current Biol (2002) 12:735-739 in which they identify 34 novel miRNAs by tissue-specific cloning of approximately 21-nucleotide RNAs from mouse (Lagos-Quintana et al., 2002).

Similarly, Michael M et al, Mol Can Res (2003) 1:882-891 describes the identification of 28 different miRNA sequences in colonic adenocarcinomas and normal mucosa.

Chen C-Z et al, Science (2004) 303:83-86 describes three miRNAs, miR-181, miR-142 and miR-223 which are specifically expressed in hematopoietic cells (Chen et al., 2004).

Sempere L et al, Genome Biology (2004) 5:R13 discloses a total of 17 miRNAs detected exclusively in a particular mouse organ; these included: seven brain-specific miRNAs (miR-9, -124a, -124b, -135, -153, -183, -219), six lung-specific miRNAs (miR-18, -19a, -24, -32, -130, -213), two spleen-specific miRNAs (miR-189, -212), one liver-specific miRNA (miR-122a), and one heart-specific miRNA (miR-208). All of the indicated mouse brain-, liver- and heart-specific miRNAs were also detected in the human counterpart organs (miRNA expression was not examined in human kidney, lung or spleen), with the exception of miR-183 in the human brain. Among the 75 miRNAs that were detected in two or more mouse organs, the levels of 14 of these were detected in a particular mouse organ at levels at least two-fold higher than in any other organ; these included: seven brain-enriched miRNAs (miR-9*, -125a, -125b, -128, -132, -137, -139), three skeletal muscle-enriched miRNAs (miR-1d, -133, -206), two kidney-enriched miRNAs (miR-30b, -30c), and one spleen-enriched miRNA (miR-99a). All brain-enriched and skeletal muscle-enriched miRNAs had similar elevated levels in the human counterpart organs. The high conservation of expression of these organ-specific and organ-enriched miRNAs between mouse and human suggests that they may play a conserved role in the establishment and/or maintenance of a cell or tissue type of that particular organ (Sempere et al., 2004).

Baskerville & Bartel, RNA (2005) 11:241-247 discloses a microarray profiling survey and the expression patterns of 175 human miRNAs across 24 different human organs. The results show that proximal pairs of miRNAs are generally coexpressed (Baskerville and Bartel, 2005). In addition, an abrupt transition in the correlation between pairs of expressed miRNAs occurs at a distance of 50 kb, implying that miRNAs separated by <50 kb typically derive from a common transcript. Some miRNAs are within the introns of host genes. Intronic miRNAs are usually coordinately expressed with their host gene mRNA, implying that they also generally derive from a common transcript, and that in situ analyses of host gene expression can be used to probe the spatial and temporal localization of intronic miRNAs.

Barad et al, Genome Research (2004) 14:2486-2494 establishes a miRNA-specific oligonucleotide microarray system that enables efficient analysis of the expression of the human miRNAs identified so far. It shows that the 60-mer oligonucleotide probes on the microarrays hybridize with labeled cRNA of miRNAs, but not with their precursor hairpin RNAs, derived from amplified, size-fractionated, total RNA of human origin. Signal intensity is related to the location of the miRNA sequences within the 60-mer probes, with location at the 5' region giving the highest signals, and at the 3' end, giving the lowest signals. Accordingly, 60-mer probes harboring one miRNA copy at the 5' end gave signals of similar intensity to probes containing two or three miRNA copies. Mismatch analysis shows that mutations within the miRNA sequence significantly reduce or eliminate the signal, suggesting that the observed signals faithfully reflect the abundance of matching miRNAs in the labeled cRNA. Expression profiling of 150 miRNAs in five human tissues and in HeLa cells revealed a good overall concordance with previously published results, but also with some differences. They present data on miRNA expression in thymus, testes, and placenta, and have identified miRNAs highly enriched in these tissues. Taken together, these results highlight the increased sensitivity of the DNA microarray over other methods for the detection and study of miRNAs, and the immense potential in applying such microarrays for the study of miRNAs in health and disease (Barad et al., 2004).

Kasashima K et al, Biochem Biophys Res Commun (2004) 322(2):403-10 describes the identification of three novel and 38 known miRNAs expressed in human leukemia cells (HL-60)(Kasashima et al., 2004).

Mansfield J et al, Nature Genetics (2004) 36:1079-1083 discloses the tissue-specific expression of several miRNAs during embryogenesis, including miR-10a and miR-196a (Mansfield et al., 2004).

Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias; the miR-15a/miR-16 locus is frequently deleted or down-regulated in patients with B cell chronic lymphocytic leukemia and miR-142 is at a translocation site found in a case of aggressive B cell leukemia. It is stated that these results indicate that miRNAs may be important regulators of mammalian hematopoiesis.

Methods of identifying new miRNAs and their target sequences using a computation approach are disclosed in WO2004/066183 and Brennecke J et al, PLoS Biology (2005) 3(3):0404-0418 (Brennecke et al., 2005).

The following table 1 summarises miRNA which may find applicability in the present invention.

TABLE 1

Expression studies on mammalian miRNAs

| Expression Pattern | miRNA | References |
|---|---|---|
| Tissue-specific expression patterns of mammalian miRNAs | | |
| ES-cell specific | miR-296 | a |
| Expressed in ES cells, but up-regulated on differentiation | miR-21 and miR-22 | a |
| Expressed in both ES cells and various adult tissues | miR-15a, miR-16, miR-19b, miR-92, miR-93 miR-96, miR-130 and miR-130b | a |
| Enriched during mouse brain development | miR-128, miR-19b, miR-9, miR-125b, miR-131 miR-178, miR-124a, miR-266 and miR-103 | b, c |
| Enriched in adult brain | miR-9*, miR-125a, miR-125b, miR-128, miR-132 miR-137, miR-139, miR-7, miR-9, mi-R124a, miR-124b, miR-135, miR-153, miR-149, miR-183, miR-190, and miR-219 | b |
| Enriched in lung | miR-18, miR-19a, miR-24, miR-32, miR-130 miR-213, miR-20, miR-141, miR-193 and miR-200b | b |
| Enriched in spleen | miR99a, miR-127, miR-142-a, miR-142-s, miR-151, miR-189b and miR-212 | b |
| Haematopoietic tissues | miR-181, miR-223, miR-155 and miR-142 | b |
| Enriched in liver | miR-122a, miR-152, miR-194, miR-199 and miR-215 | b |
| Enriched in heart | miR-1b, miR-1d, miR-133, miR-206, miR-208 and miR-143 | b |
| Enriched in kidney | miR-30b, miR-30c, miR-18, miR-20, miR-24 miR-32, miR-141, miR-193 and miR-200b | b |

TABLE 1-continued

Expression studies on mammalian miRNAs

| Expression Pattern | miRNA | References |
|---|---|---|
| Ubiquitously expressed | miR-16, miR-26a, miR-27a, miR-143a, miR-21 let-7a, miR-7b, miR-30b and miR-30c | b |
| Abnormal miRNA expression during tumorigenesis | | |
| Downregulated in chronic Lymphocytic leukaemias | miR-15 and miR-16 | d |
| Downregulated in lung cancer cell lines | miR-26a and miR-99a | e |
| Downregulated in colon Cancers | miR143/miR-145 cluster | f |
| Upregulated in Burkitt Lymphoma ES cells, embryonic stem cells. | miR-155 | g | a Houbaviy et al, Dev. Cell (2003) 5: 351-358.
b Sempere et al, Genome Biol. (2004) 5, R13.
c Krichevsky et al, RNA (2003), 9: 1274-1281.
d Calin et al, Proc Natl Acad Sci (2002) 99: 15524-15529.
e Calin et al, Proc Natl Acad Sci (2004) 101: 2999-3004.
f Michael et al, Mol Cancer Res (2003) 1: 882-891.
g Metzier et al, Genes Chromosomes Cancer (2004) 39: 167-169.

Although our data demonstrates the utility of this approach for restricting expression from hematopoeitic cells, the endogenous miRNA regulatory network will enable many more possibilities for tightly restricting transgene expression. Expression studies have already revolved miRNAs specific for many different cell types, including neurons, pancreatic islets, and adipose tissue. Using our design, a vector could be created which includes target sequences of miR-21 and miR-22, two miRNAs upregulated following embryonic stem cell (ESCs) differentiation (Houbaviy et al., 2003), tethered to a suicide gene such as thymidine kinase. This vector could serve to selectively kill undifferentiated ESCs in ESC-derived tissue, a much desired safety control for bringing ESC-based therapies to the clinic.

Another possible use of the miRNA-regulated vector design would be in the treatment of cancer. Several reports have indicated that specific miRNAs are downregulated in certain tumors. miR-15 and mir-45, for example, is downregulated in chronic lymphocytic leukaemias and breast cancer (Cahn et al., 2004a; Cahn et al., 2004b; Iorio et al., 2005). The miR-15 or mir-145 target sequence could be included in a vector expressing a toxic transgene. Normal cells expressing miR-15 or mir-145, including vector producing cells, would suppress production of the toxin and thus survive, whereas transduced tumor cells, no longer expressing miR-15 or mir-145, would readily produce the toxin gene and die.

The miRNA vector may be used in conjunction with a bidirectional promoter (Amendola et al., 2005). These vectors, which have the unique property that they produce two distinct mRNA transcripts from a single promoter, can be modified to include miRNA target sequences in one or both of the expression cassettes. Thus, addition of mir-142-3pT to transgene 1, but not transgene 2, would enable ubiquitous expression of transgene 2, while preventing expression of transgene 1 in hematopoeitic cells. This design will enable divergent regulation of two transgenes, a feat not possible with current technologies.

The miRNA may be used with a gene vector suitable for transient expression of the transgene. Viral vectors for use in the invention include but are not limited to integration defective retroviral vectors, integration defective lentiviral vectors (IDLV), integration defective spuma/foamy vectors, herpes viral vectors, baculoviral and SV-40-based vectors, and hybrid vectors made by a combination of non-viral and/or viral components derived from the above mentioned or other types of viral vectors.

Retroviral and Lentiviral Vectors

The retroviral vector of the present invention may be derived from or may be derivable from any suitable retrovirus. A large number of different retroviruses have been identified. Examples include: murine leukemia virus (MLV), human T-cell leukemia virus (HTLV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al. (1997) "Retroviruses", Cold Spring Harbour Laboratory Press Eds: J M Coffin, S M Hughes, H E Varmus pp 758-763.

Retroviruses are RNA viruses that replicate through an integrated DNA intermediate. Retroviral particles encapsidate two copies of the full-length viral RNA, each copy containing the complete genetic information needed for virus replication. Retroviruses possess a lipid envelope and use interactions between the virally encoded envelope protein that is embedded in the membrane and a cellular receptor to enter the host cells. Using the virally encoded enzyme reverse transcriptase, which is present in the virion, viral RNA is reverse transcribed into a DNA copy. This DNA copy is integrated into the host genome by integrase, another virally encoded enzyme. The integrated viral DNA is referred to as a provirus and becomes a permanent part of the host genome. The cellular transcriptional and translational machinery carries out expression of the viral genes. The host RNA polymerase II transcribes the provirus to generate RNA, and other cellular processes modify and transport the RNA out of the nucleus. A fraction of viral RNAs are spliced to allow expression of some genes whereas other viral RNAs remain full-length. The host translational machinery synthesizes and modifies the viral proteins. The newly synthesized viral proteins and the newly synthesized full-length viral RNAs are assembled together to form new viruses that bud out of the host cells.

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al (1997) ibid.

The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

In a typical retroviral vector of the present invention, at least part of one or more protein coding regions essential for replication may be removed from the virus. This makes the viral vector replication-defective.

The retroviral vector of the present invention in intergration defective. Such a vector can be produced, for example, by packaging the vector with catalytically inactive integrase (such as an HIV integrase bearing the D64V mutation in the catalytic site; Naldini et al., Science 1996, and PNAS USA 1996, Leavitt et al. J Virol. 1996) or by deleting essential att sequences from the vector LTR (Nigthingale et al. Mol Ther 2006), or by a combination of the above. These modifications reduce integration to baseline level leaving unaffected the other steps of the transduction process (Naldini et al. Science 1996, Nigthingale et al. Mol Ther 2006, Vargas et al. Hum Gene Ther 2004, Yáñez-Muñoz et al. Nat Med 2006; Philippe et al. PNAS 2006).

Lentivirus vectors are part of a larger group of retroviral vectors. A detailed list of lentiviruses may be found in Coffin et al (1997) "Retroviruses" Cold Spring Harbour Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

The lentivirus family differs from retroviruses in that lentiviruses have the capability to infect both dividing and non-dividing cells.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "non-primate" vector, i.e., derived from a virus which does not primarily infect primates, especially humans.

The examples of non-primate lentivirus may be any member of the family of lentiviridae which does not naturally infect a primate and may include a feline immunodeficiency virus (My), a bovine immunodeficiency virus (BIV), a caprine arthritis encephalitis virus (CAEV), a Maedi visna virus (MVV) or an equine infectious anaemia virus (EIAV).

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

It has also been demonstrated that the HIV-1 vector can be propagated to high viral titers using viral proteins from simian immunodeficiency virus. In one system, the vector and helper constructs are from two different viruses, and the reduced nucleotide homology may decrease the probability of recombination. In addition to vectors based on the primate lentiviruses, vectors based on feline immunodeficiency virus have also been developed as an alternative to vectors derived from the pathogenic HIV-1 genome. The structures of these vectors are also similar to the HIV-1 based vectors.

Preferred vectors of the present invention have sufficient retroviral genetic information to allow packaging of an RNA genome, in the presence of packaging components, into a viral particle capable of infecting a target cell but is incapable of independent replication to produce infectious retroviral particles within the final target cell. Preferably the vector lacks a functional gag-pol and/or env gene and/or other genes essential for replication.

However, the plasmid vector used to produce the viral genome within a host cell/packaging cell will also include transcriptional regulatory control sequences operably linked to the retroviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter.

Vectors Derived from Spumaviruses

Foamy viruses are unconventional retroviruses in that many features in their replication cycle are different from those of oncoviruses and lentiviruses. Although these viruses can be toxic to cultured cells, none of the foamy viruses are known to cause any disease in hosts.

An example of a foamy virus vector contains the typical retroviral cis-acting sequences. In addition to the sequences in the 5' untranslated region, the 5' portion of the gag open reading frame and sequences in the 3' portion of the pol open reading frame are important for efficient packaging. Similar to the lentiviruses, expression from the human foamy virus promoter is activated by the viral protein Tas.

Packaging Sequence

As utilized within the context of the present invention the term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles. As an example, for the Murine Leukemia Virus MoMLV, the minimum core packaging signal is encoded by the sequence (counting from the 5' LTR cap site) from approximately nucleotide 144, up through the Pst I site (nucleotide 567). The extended packaging signal of MoMLV includes the sequence beyond nucleotide 567 up through the start of the gag/pol gene (nucleotide 621), and beyond nucleotide 1040 (Bender et al. (1987)). These sequences include about a third of the gag gene sequence.

Feline immunodeficiency virus (FIV) RNA encapsidation determinants have been shown to be discrete and non-continuous, comprising one region at the 5' end of the genomic mRNA (R-U5) and another region that mapped within the proximal 311 nt of gag. (Kaye et al. (1995)) showed that mRNAs of subgenomic vectors as well as of full-length molecular clones were optimally packaged into viral particles and resulted in high-titer FIV vectors when they contained only the proximal 230 nucleotides (nt) of gag. Further 3' truncations of gag sequences progressively diminished encapsidation and transduction. Deletion of the initial ninety 5' nt of the gag gene abolished mRNA packaging, demonstrating that this segment is indispensable for encapsidation.

Herpes Viral Vectors

1. Viral Strains

The HSV vectors of the invention may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 90%, even more preferably 95%.

The use of HSV strains in therapeutic procedures will require the strains to be attenuated so that they cannot establish a lytic cycle. In particular, if HSV vectors are to be used for gene therapy in humans the polynucleotide should preferably be inserted into an essential gene. This is because if a vector virus encounters a wild-type virus transfer of a heterologous gene to the wild-type virus could occur by recombination. However as long as the polynucleotide is inserted into an essential gene this recombinational transfer would also delete the essential gene in the recipient virus and prevent 'escape' of the heterologous gene into the replication competent wild-type virus population.

Attenuated strains may be used to produce the HSV strain of the present invention, here given as examples only, including strains that have mutations in either ICP34.5 or ICP27, for example strain 1716 (MacLean et al., 1991, J Gen Virol 72: 632-639), strains R3616 and R4009 (Chou and Roizman, 1992, PNAS 89: 3266-3270) and R930 (Chou et al., 1994, J. Virol 68: 8304-8311) all of which have mutations in ICP34.5, and d27-1 (Rice and Knipe, 1990, J. Virol 64: 1704-1715) which has a deletion in ICP27. Alternatively strains deleted for ICP4, ICPO, ICP22, ICP6, ICP47, vhs or gH, with an inactivating mutation in VMW65, or with any combination of the above may also be used to produce HSV strains of the invention.

The terminology used in describing the various HSV genes is as found in Coffin and Latchman, 1996. Herpes simplex virus-based vectors. In: Latchman DS (ed). Genetic manipulation of the nervous system. Academic Press: London, pp 99-114.

2. Complementing Cell Lines

HSV viruses defective in ICP27 are propagated in a cell line expressing ICP27, for example V27 cells (Rice and Knipe, 1990, J. Virol 64: 1704-1715) or 2-2 cells (Smith et al., 1992, Virology 186: 74-86). ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27 mutant HSV strains, using methods known to those skilled in the art (for example as described in Rice and Knipe, 1990).

Cell lines which do not allow reversion of an ICP27 mutant HSV strain to a strain with functional ICP27 are produced as described above, ensuring that the vector comprising a functional ICP27 gene does not contain sequences that overlap with (i.e. are homologous to) sequences remaining in the ICP27⁻ mutant virus.

Where HSV strains of the invention comprise inactivating modifications in other essential genes, for example ICP4, complementing cell lines will further comprise a functional HSV gene which complements the modified essential gene in the same manner as described for ICP27.

3. Methods of Mutation

HSV genes may be rendered functionally inactive by several techniques well known in the art. For example, they may be rendered functionally inactive by deletions, substitutions or insertions, preferably by deletion. Deletions may remove portions of the genes or the entire gene. Inserted sequences may include the expression cassette described above.

Mutations are made in the HSV strains by homologous recombination methods well-known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

Mutations may also be made in other HSV genes, for example genes such as ICPO, ICP4, ICP6, ICP22, ICP47, VMW65, gH or vhs. In the case of the VMW65 gene, the entire gene is not deleted since it encodes an essential structural protein, but a small inactivating insertion is made which abolishes the ability of VMW65 to transcriptionally activate IE genes (Ace et al., 1989, J Virol 63: 2260-2269).

4. HSV Strains Comprising a Transgene and miRNA of the Invention

A transgene and mircoRNA of the invention may be inserted into the HSV genome at any location provided that the virus can still be propagated, which may require the use of a cell line carrying another HSV essential gene (as described in 2.) if the NOI is inserted into an essential gene The sequences of the invention may be inserted into the HSV genome by homologous recombination of HSV strains with, for example, plasmid vectors carrying the expression cassette flanked by HSV sequences, as described above for introducing mutations. The polynucleotide may be introduced into a suitable plasmid vector comprising HSV sequences using cloning techniques well-known in the art.

Diseases

The delivery of one or more therapeutic genes by a vector system according to the present invention may be used alone or in combination with other treatments or components of the treatment.

The vector of the present invention may be used for the prevention and treatment of inflammatory diseases characterized by an antigen specific immune response. In particular, in the context of autoimmune diseases (including diabetes), allergic diseases and in Protein/Enzyme Replacement Therapies including protein deficiencies, blood clotting disorders, lysosomal storage diseases such as mucopolisaccharidosis disorders.

The vector of the present invention may be used to deliver one or more transgene(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the vector of the present invention may be used to deliver one or more transgene(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the retroviral vector of the present invention may be used to deliver one or more transgenes(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

In a preferred embodiment, the autoimmune disease is diabetes. The vector of the present invention may be used for inducing or enhancing immunological tolerance to insulin-secreting pancreatic B-cells.

Insulin Dependent Diabetes Mellitus Human type I or insulin-dependent diabetes mellitus (IDDM) is characterized by autoimmune destruction of the cells in the pancreatic islets of Langerhans. The depletion of cells results in an inability to regulate levels of glucose in the blood. Overt diabetes occurs when the level of glucose in the blood rises above a specific level, usually about 250 mg/di. In humans a long presymptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (IA2), each an example of a self-protein used in the present invention.

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration.

The Non-Obese Diabetic (NOD) mouse is an animal model with many clinical, immunological, and histopathological features in common with human IDDM. NOD mice spontaneously develop inflammation of the islets and destruction of the cells, which leads to hyperglycemia and overt diabetes. It has been shown that administration of insulin or GAD, as proteins, or of peptides derived from these proteins, under tolerizing conditions to NOD mice prevents disease and down-regulates responses to the other self-antigens.

Autoantigens targeted in human insulin dependent diabetes mellitus may include the self-protein (s) insulin, insulin β chain, preproinsulin, proinsulin, glutamic acid decarboxylase 65 kDa and 67 kDa forms, tyrosine phosphatase IA2 or IA-2b, carboxypeptidase H, heat shock proteins, glima 38, islet cell antigen 69 kDa, p52, GT3, GM2-1 and islet cell glucose transporter (GLUT 2) or of peptides derived from these proteins. Preferably the self protein is an insulin β chain which displays epitopes of MHC class I and II for induction of tolerance in diabetes. In one embodiment the transgene is insulin β chain 9-23 peptide.

In another embodiment the vector of the present invention may be used for induction of tolerance to a viral antigen such as in the context of organ transplantation in patients infected with hepatitis C virus (HCV). In this embodiment the transgene may encode a viral antigen, preferably an HCV antigen. HCV causes chronic hepatitis, and is the main cause of cirrhosis and hepatocellular carcinoma (HCC) in Western countries and the most common indication for liver transplantation worldwide (Toniutto et al 2008; Berenguer et al 2000). Studies have shown a reduced rate of patient and graft survival in patients testing positive for anti-HCV antibody prior to transplantation or undergoing transplantation for HCV-related cirrhosis (Bruchfeld et al 2004; Gentil et al 1999), and HCV infection of the graft occurs in most liver transplants (Toniutto et al 2008). Current strategies to prevent or slow the development of HCV-related graft failure include anti-viral therapy prior to transplantation, or post-transplantation therapy both before and after the development of acute hepatitis. However, these treatments often result in a low virologic response or a higher risk of organ rejection (Arjal et al 2007) and there is a need for improved therapies to protect the transplanted organ and patient.

The delivery of one or more therapeutic genes by a vector system according to the invention may be used alone or in combination with other treatments or components of the treatment.

Preferred diseases which may be treated by the vector include, but are not limited to: cancer, neurological diseases, inherited diseases, heart disease, blood clotting deficiencies, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, blood clotting factors, vasoactive proteins or peptides, cytokines, chemokines, anti-viral proteins, antisense RNA and ribozymes.

The present invention also provides a pharmaceutical composition for treating an individual by gene therapy, wherein the composition comprises a therapeutically effective amount of the vector of the present invention comprising one or more deliverable therapeutic and/or diagnostic transgenes(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

EXAMPLES

We have developed a novel strategy to enable stable gene transfer in immunocompent mice which relies on micro- RNA-mediated post-transcriptional regulation of transgene expression. In this strategy, we incorporate complementary sequences to hematopoietic-specific microRNAs, such as miR-142 (142T), into the 3' untranslated region of lentiviral vectors (LV), making the transgene-encoding transcript susceptible to miRNA-mediated down-regulation. In this way, transgene expression is specifically prevented in hematopoietic-lineage antigen presenting cells (APC), while being maintained in non-hematopoietic cells (Brown et al., Nat Med 2006). This strategy, which imposes a stringent post-transcriptional control on transgene expression, enabled stable delivery and long-term expression of transgenes encoding GFP, as well as human coagulation Factor IX (FIX), in immunocompetent mice, without evidence of immune response to the transgene product (Brown et al., Blood 2007). We have found that miR-142 regulation not only prevents immune-mediated clearance of transduced cells, but also induces antigen-specific Regulatory T cells (T regs) and mediates robust immunological tolerance to the transgene-encoded antigen, which could not be reversed by vaccination (data not shown). Induction of antigen-specific T regs and immune tolerance were remarkable findings, given that the transgene-encoded GFP represented an exogenous neo-antigen for the treated mice. The mechanism(s) underlying this response are still unclear and currently under investigation, although our preliminary findings indicate that a combination of the following factors is required to achieve this outcome: i) miRNA-mediated de-targeting of transgene expression from hematopoietic lineage cells in the liver and spleen; ii) transgene expression driven by the vector either specifically in hepatocytes or reaching high-levels in non-hematopoietic cells of a peripheral organ. Moreover, continuous transgene expression in these sites may be required for maintaining this response.

Since insertional mutagenesis is a concern for integrating vectors, we have explored the potential advantages of the use of integration defective (in this case, integrase-defective) LV (IDLV) to express transgenes in tissues characterized by slow turnover, such as the liver. IDLV can be produced either by packaging the vector with catalytically inactive integrase (such as an HIV integrase bearing the D64V mutation in the catalytic site; Naldini et al., Science 1996, and PNAS USA 1996, Leavitt et al. J Virol. 1996) or by deleting essential att sequences from the vector LTR (Nigthingale et al. Mol Ther 2006), or by a combination of the above. These modifications reduce integration to baseline level leaving unaffected the other steps of the transduction process (Naldini et al. Science 1996, Nigthingale et al. Mol Ther 2006, Vargas et al. Hum Gene Ther 2004, Yáñez-Muñoz et al. Nat Med 2006; Philippe et al. PNAS 2006). Upon transduction, IDLV can drive low-level transgene expression from the non-integrated proviral forms which transiently accumulate in transduced cells. Because this episomal DNA is progressively lost in actively dividing cells, transgene expression is only transient in proliferating cells (Naldini et al. PNAS USA 1996; Lombardo et al. Nat Biotechnol 2007). On the other hand, IDLV have been more recently reported to drive prolonged transgene expression in some quiescent mouse tissues, such as the retina and central nervous system neurons, presumably because the episomal DNA remains associated with the post-mitotic nucleus or for other unknown reasons (Yáñez-Muñoz et al. Nat Med 2006; Philippe et al. PNAS 2006). However, the actual extent and duration of transgene expression remain unclear, and are likely to be affected by the targeted tissue.

We set out to evaluate IDLV-derived transgene expression in the liver. To this aim we administered intravenously to normal adult mice matched doses of integrase-competent LV or IDLV encoding GFP under the control of the hepatocyte-specific ET promoter and carrying target sequences for miR-142 (ET.142T; FIG. 1A) (Brown et al., 2007). A total of four cohorts of mice have been injected with 40 or 20 µg HIV-1 capsid p24 of LV or IDLV (different vector preparations) in two different experiments and the mice were euthanized at the indicated time points post-injection to monitor transgene expression in hepatocytes and liver DNA vector content (FIG. 1).

Figure 1B:
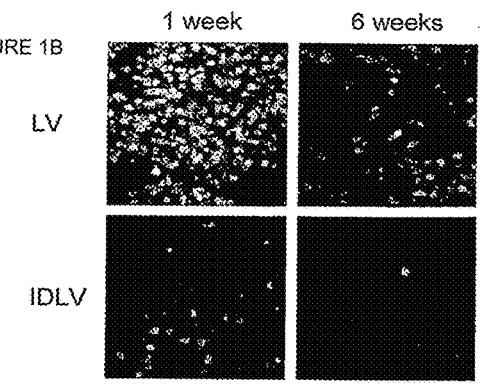
Figure 1C:
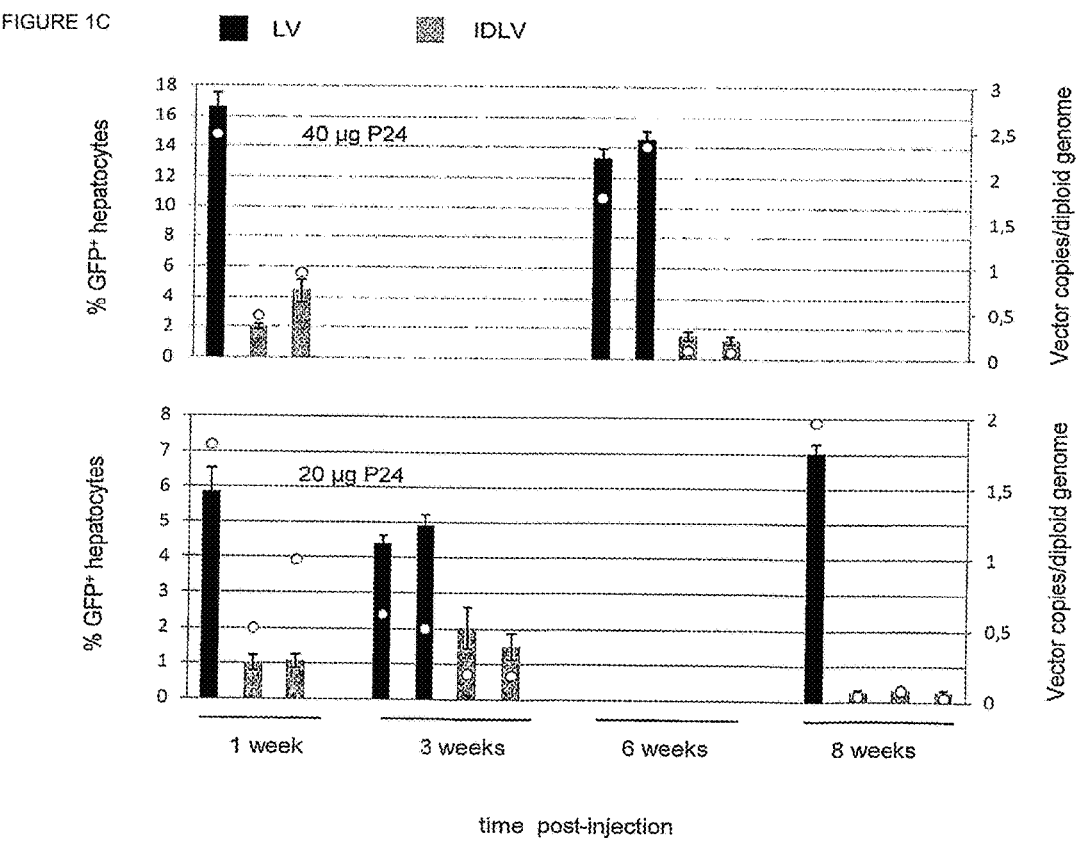

At 1 week post-injection we found detectable GFP expression (by direct fluorescence microscopy) in the liver of IDLV-treated mice but to a much lesser extent than that observed in the liver of mice treated with the integrating LV counterpart (FIG. 1B). Using an anti-GFP immunostaining, which amplifies the GFP signal in low-expressing cells, we were able to verify that a significant proportion of hepatocytes in IDLV-treated mice expressed GFP to levels barely detectable by direct fluorescence. Morphometric analysis in immunostained slides showed from 1 to 4% of GFP$^+$ hepatocytes in the liver of IDLV-treated mice depending on the dose used, while from 6 to 16% of hepatocytes were found to be positive in the mouse receiving a matched dose of the integrase-competent vector (FIG. 1C). Measurement of vector copy number (VCN) showed comparable amount of vector DNA in the liver of treated mice, although IDLV-treated mice presented slightly lower vector content which may be due to less efficient transduction or lower episomal DNA recovery from liver lysates (FIG. 1C).

Unexpectedly, however, at 6 weeks post-injection, GFP expression was drastically reduced in IDLV-treated mice while it remained stable in those injected with LV. Livers of the latter group presented around 14% of GFP$^+$ hepatocytes with no overt decrease as compared to those obtained at 1 week after injection. In contrast, morphometric analysis in livers of IDLV-treated mice at 6 weeks post-injection resulted in 2-4 fold lower GFP$^+$ hepatocytes than in those obtained at 1 week (FIG. 1C top panel). VCN evaluation showed that the integrating vector DNA is maintained over time while the IDLV content was reduced to very low levels (FIG. 1C top panel).

Due to the limited number of mice analyzed, we repeated the experiment to confirm our results. More mice were injected with 20 µg p24 of LV or IDLV as above and morphometric and VCN analysis was performed at 1, 3 and 8 weeks post-injection to better monitor transgene expression and vector DNA kinetics in vivo. These analyses showed that transgene expression originating from integrase-competent LV is stable over time as well as vector content, with GFP$^+$ hepatocytes ranging from 4 to 7% and VCN between 0.5 and 2 vector copies/diploid genome, as expected from previous data (FIG. 1C bottom panel). In striking contrast, IDLV-derived transgene expression was reduced to almost undetectable levels and vector DNA was reduced to very low levels (ranging from 0.04 to 0.08 copies/diploid genome) at 8 weeks after vector injection (FIG. 1C bottom panel).

These data indicate that IDLV can drive low-level transgene expression, which decreases over time in the liver of adult mice. Moreover, although still detectable at low levels, IDLV DNA is strongly reduced over time and residual forms are known to be mostly episomal (data not shown). Based on these results, we reasoned that this platform could be suitable to generate tolerance to a specific antigen for immunomodulatory purposes.

Figure 2A:
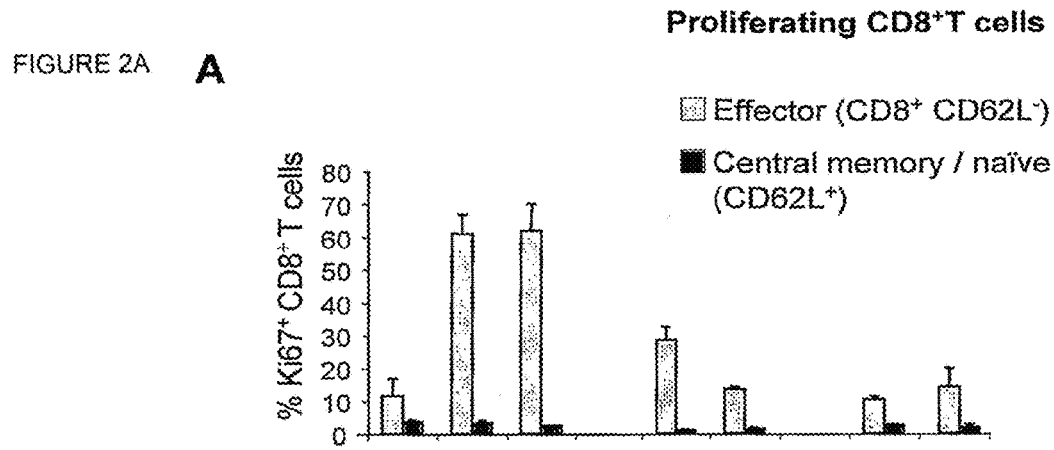
Figure 2B:
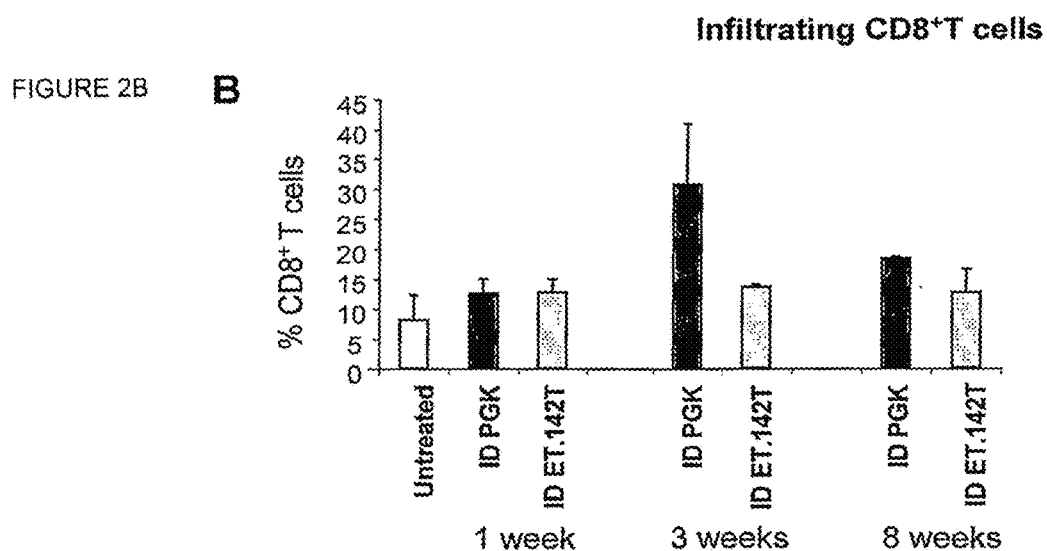
Figure 2C:
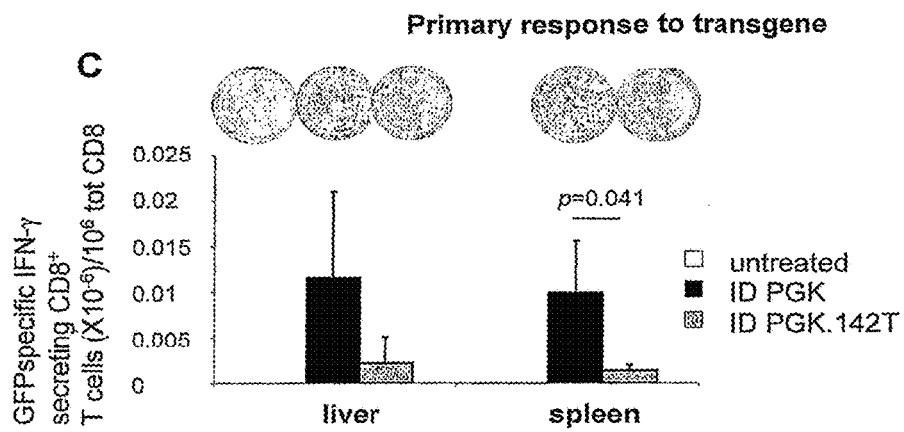

To define whether transgene tolerance can be induced, as described for the integrase competent LV gene transfer model (Annoni et al., 2009), CD8+ T cells response was studied in the liver of ID-ET.142T- and ID-PGK-treated mice. Mononuclear cells (MNC) were isolated from the liver at 1, 3, and 8 weeks after IDLV injection and the frequency of proliferating effector CD8+CD62L− T cells was determined. Well-detectable CD8+ T cells proliferation occurred 1 week after IDLV treatment independently from the presence or absence of miR-142-mediated transgene regulation. However, CD8+ T cells proliferation returned to normal levels by the third week only in ID-ET.142T treated mice. Conversely, rate of proliferation of CD8+ T cell in the liver of ID-PGK control mice remained elevated even at the third week post injection (FIG. 2A). Furthermore, the extent of T cells liver infiltration was evaluated in parallel, indicating that the CD8+ T cells proliferation phase in ID-PGK-treated mice led to a clear CD8+ T cells accumulation 3 weeks post IDLV injection. These results showed that miR-142 regulation of antigen (Ag) expression generate transient CD8+ T effector cells expansion, which rapidly contracts and only produces a mild increase in CD8+ T cells accumulation in the liver (FIG. 2B). These findings indicate that presentation of the IDLV-encoded Ag to immune cells is preserved by miR-142 regulation but its pattern is changed in still unknown way to change the outcome of the response. Transgene-specific primary response was studied enumerating IFN-γ producing CD8+ T cells in response to transgene-specific stimulation. ID-PGK treatment generated higher number of transgene specific CD8+ T cells both in the spleen and in the target organ (FIG. 2C), indicating that the pattern of transgene expression generated by miR-142 regulation drastically reduced the immunogenicity of IDLY-mediated gene transfer, and likely overturn it from the induction of Ag-specific immunity to the induction of Ag-specific tolerance, as we previously demonstrated for the delivery of integrase-competent LV.

Figure 2D:
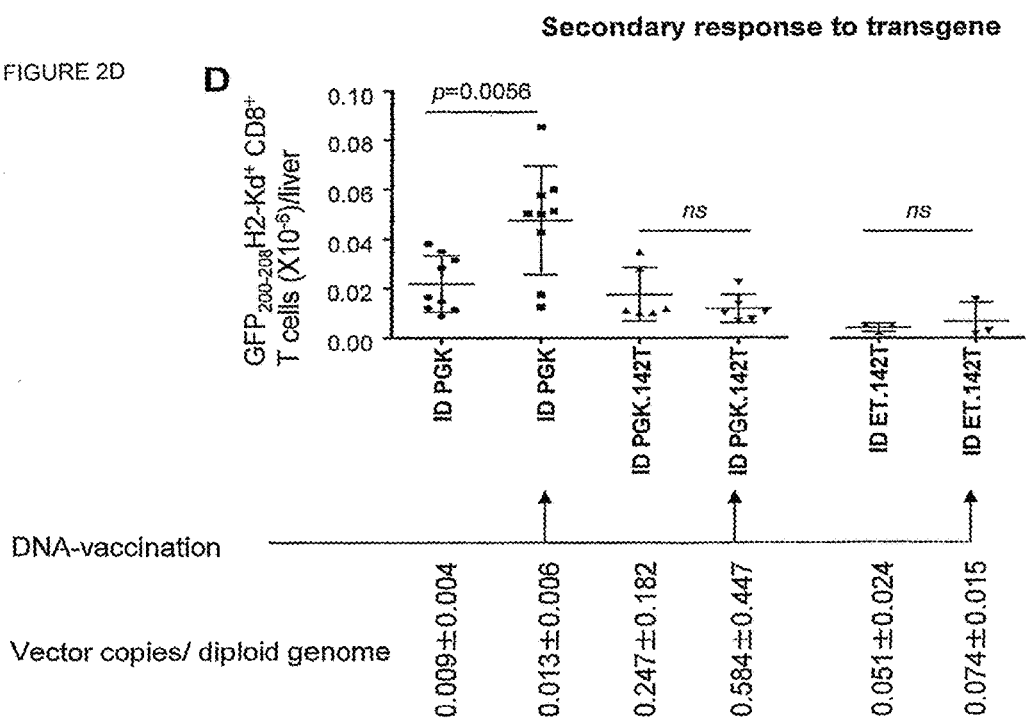

Six weeks after IDLV treatment mice were Ag re-challenged, by GFP-encoding plasmid intramuscular injection, to evaluate the induction of secondary anti-transgene immune response. Secondary expansion of transgene-specific CD8+ T cells was detectable in ID-PGK-injected mice only, indicating that those mice maintained GFP responsiveness. On the contrary, the absence of response to transgene indicated that both ID-PGK.142T and ID-ET.142T treatment generated a state of transgene-specific immunological tolerance in recipient mice. In addition, residual levels of vector DNA were detected only in mice receiving ID-PGK.142T and ID-ET.142T, while transduced hepatocytes in those treated with ID.PGK control vector were completely cleared (FIG. 2D).

Overall, these data confirm and consolidate the ones previously submitted, indicating that single administration of miR-142-regulated IDLV can tolerize treated mice towards the encoded protein, avoiding the risks of insertional mutagenesis.

Materials and Methods:
Vectors Construction and Animal Procedures:

Construction of pCCLsin.cPPT.PGK.GFP.wpre.142T, pCCLsin.ET.GFP.wpre.142T, pCCLsin.ET.hFIX.wpre.142T has been previously described (Brown et al., 2007; Brown et al., 2006). The integrase-defective third generation packaging plasmid pMDLg/p.RRE.D64VInt was generated by replacing the BclI-AflII fragment from plasmid pCMVDR9-D64V (Naldini et al., 1996). Third-generation lentiviral vectors (LV) were produced by $Ca_3PO_4$ transfection into 293T cells. Briefly, supernatants were collected, passed through a 0.22 μm filter, and purified by ultracentrifugation as described (Brown et al., 2007). Transducing units (TU) for integrating vectors encoding enhanced green fluorescent protein (GFP) was determined on 293T cells. Vector particles were measured by HIV-1 Gag p24 antigen immunocapture according to the manufacturer's protocol (NEN Life Science Products, Boston, Mass.), as previously described (Follenzi et al., 2004). Vector administration was carried out by tail vein injection on 6-8 weeks old mice. DNA vaccination was performed as previously described (Kakimi et al., 2002). Briefly, 0.5 nmol of Cardiotoxin-1 (Sigma, St Louis, Mo.) were injected in triadic leg muscles. Five days later, mice were injected again in the same position with 50 μg/leg of pCCLsin.cPPT.CMV.GFP.wpre plasmid. Mice were euthanized 12 days after DNA administration. All the animal procedures were performed accordingly to protocols approved by Hospital San Raffaele Institutional Animal Care and Use Committee (IACUC #321).

Tissue Analysis:

Treated mice were euthanized at the indicated time points after LV/IDLV injection and the liver was fixed in 4% paraformaldehyde, embedded in optimal cutting temperature (OCT), and frozen. Cryostat sections (10 μm thick) were blocked with 5% goat serum (Vector laboratories, Burlingame, Calif.), 1% bovine serum albumine (BSA), 0.1% Triton X-100 in PBS, and directly analyzed by 3-laser confocal microscope (Radiance 2100, Bio-Rad, Hercules, Calif.) or incubated with rabbit anti-GFP (Molecular Probe; Eugene, Oreg.). Sections were washed and incubated with (FITC)-conjugated goat anti-rabbit immunoglobulin G. Nuclei were stained with TOPRO-3 (Molecular Probe). Fluorescent signals from single optical sections were acquired by 3-laser confocal microscope (Radiance 2100, Bio-Rad, Hercules, Calif.). Morphometric analysis was performed by counting GFP+ and total hepatocytes in 5 different fields of 6-8 non-consecutive liver sections per mice.

DNA Analysis:

Genomic DNA from tissues was extracted by using Maxwell™ 16 DNA extraction kit (Promega), according to manufacturer's instructions. Vector copy number (VCN) was quantified by quantitative PCR (Q-PCR) using the primer and probe set previously described (Brown et al., 2006). All Reactions were carried in triplicate in an ABI Prism 7900 (Applied Biosystems).

Cell Preparation:

Mice were euthanized at the necessary time point, and spleens were collected and processed into single cell suspension. Splenic CD8+ T cells were magnetically isolated from splenocytes by negative selection kit (Miltenyi Biotec, Bergisch Gladbach, Germany). Intra-hepatic leukocytes (IHL), which include T cell infiltrates, were isolated from the liver by smashing the tissue and running the sample on a Percoll (Sigma) gradient, as previously described (Liu et al., 2000).

Fluorescence-Activated Cell Sorting Analysis:

Spleen and IHLs were stained with the following monoclonal antibodies (mAb): Peridinin Chlorophyll (PerCP) conjugated anti-CD8a (53-6.7); Pacific Blue (PB) conjugated anti-CD4 (RM4-5), R-phycoerythrin (PE) conjugated anti-CD62L (MEL14), flourescein-isothiocyanate (FITC) anti-Ki-67 (B56) (BD Biosciences, Mountain View, Calif.). Detection of GFP-specific CD8+ T cells was performed by APC labeled ProS MHC pentamer H-2K$^d$ HYLSTQSAL (GFP200-208) according to the manufactures instructions (Proimmune, Oxford, UK). Labeled cells were analyzed with a FACSCanto flow cytometer equipped with Diva software (BD Biosciences).

IFN-γ ELISPOT Assay:

IFN-γ secreting cells were enumerated by enzyme-linked immunospot (ELISPOT) assay in response to GFP expressing cells. Briefly, $5 \times 10^4$ isolated splenic CD8$^+$ T cells were plated in ELISPOT plates (Millipore, Badford, Mass.) coated with anti-IFN-γ capture mAb (2.5 µg/ml, R46A2; BD) in the presence of IL-2 (50 U/mL; BD Biosciences, Mountain View, Calif.), and $5 \times 10^4$ irradiated (30Gy) wtP815 or GFP$^+$P815 cells. After 42 hrs of incubation at 37° C., 5% $CO_2$, the plates were washed, and IFN-□ producing cells were detected by anti-IFN-γ detection mAb (0.5 µg/mL, XMG 1.2; BD). Spots were counted by ELI.Expert.Elispot-Reader and analyzed by Eli.Analyse software (A.EL.VIS, Hannover, Germany).

Statistical Analysis:

Statistical analyses were performed using the Mann-Whitney test.

These data demonstrate that IDLY encoding a miR-142-regulated transgene mediate a long-lasting and robust state of immunological tolerance, which cannot be broken by re-challenge with the antigen. Together these data show that transiently expressing antigens by IDLV in the liver results in either effective immunization or active tolerance, depending on the way transgene expression is regulated by vector design.

These results demonstrate a new strategy of tolerance induction which exploits miR-142-regulation in combination with transient gene delivery. Surprisingly, transgene expression, albeit only reaching low levels and being short-term, leads to a robust state of immunological tolerance, which is maintained also when transgene expression is virtually lost in the target tissues. Because IDLV express the transgene transiently in the liver and the vector itself is lost after few weeks, this strategy allows inducing long-lasting tolerance to transgene-encoded antigens without the need for long-term transgene expression and the risks associated with vector integration.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Ace et al., 1989, J Virol 63: 2260-2269

Amendola, M., Venneri, M. A., Biffi, A., Vigna, E., and Naldini, L. (2005). Coordinate dual-gene transgenesis by lentiviral vectors carrying synthetic bidirectional promoters. Nat Biotechnol 23, 108-116.

Annoni A, Brown B D, Cantore A, Sergi Sergi L, Naldini L, Roncarolo M G. In vivo delivery of a microRNA regulated transgene induces antigen-specific regulatory T cells and promotes immunological tolerance. Blood. 2009.

Arjal, R. R., Burton J R, J. R., Villamil, F., and Rosen, H. R. (2007) Review Article: the treatment of hepatitis C virus recurrence after liver transplantation. Aliment Pharmacol Ther 26, 127-140.

Barad, O., Meiri, E., Avniel, A., Aharonov, R., Barzilai, A., Bentwich, I., Einav, U., Gilad, S., Hurban, P., Karov, Y., et al. (2004). MicroRNA expression detected by oligonucleotide microarrays: system establishment and expression profiling in human tissues. Genome Res 14, 2486-2494.

Baskerville, S., and Bartel, D. P. (2005). Microarray profiling of microRNAs reveals frequent coexpression with neighboring miRNAs and host genes. RNA 11, 241-247.

Berenguer, M., Ferrell, L., Watson, J., Prieto, M., Kim, M., Rayon, M., Cordoba, J., Herola, A., Ascher, N., Mir J., et al (2000) HCV-related fibrosis progression following liver transplantation: increase in recent years. J Hepatol 32, 673-684.

Brown B D, Venneri M A, Zingale A, Sergi Sergi L, Naldini L. (2006) Endogenous microRNA regulation suppresses transgene expression in hematopoietic lineages and enables stable gene transfer. Nat Med. May; 12(5):585-91. Epub 2006 Apr. 23.

Brennecke, J., Stark, A., Russell, R. B., and Cohen, S. M. (2005). Principles of microRNA-target recognition. PLoS Biol 3, e85.

Brown, B. D., and Lillicrap, D. (2002). Dangerous liaisons: the role of "danger" signals in the immune response to gene therapy. Blood 100, 1133-1140.

Brown, B. D., Shi, C. X., Powell, S., Hurlbut, D., Graham, F. L., and Lillicrap, D. (2004a). Helper-dependent adenoviral vectors mediate therapeutic factor VIII expression for several months with minimal accompanying toxicity in a canine model of severe hemophilia A. Blood 103, 804-810.

Brown, B. D., Shi, C. X., Rawle, F. E., Tinlin, S., McKinven, A., Hough, C., Graham, F. L., and Lillicrap, D. (2004b). Factors influencing therapeutic efficacy and the host immune response to helper-dependent adenoviral gene therapy in hemophilia A mice. J Thromb Haemost 2, 111-118.

Brown B D, Cantore A, Annoni A, et al. A microRNA-regulated lentiviral vector mediates stable correction of hemophilia B mice. Blood. 2007; 110:4144-4152.

Bruchfeld, A., Wilczek, H., and Elinder, C.-G. (2004) Hepatitis C infection, time in renal-replacement therapy, and outcome after kidney transplantation. Transplantation 78, 745-750.

Calin, G. A., Liu, C. G., Sevignani, C., Ferracin, M., Felli, N., Dumitru, C. D., Shimizu, M., Cimmino, A., Zupo, S., Dono, M., et al. (2004a). MicroRNA profiling reveals distinct signatures in B cell chronic lymphocytic leukemias. Proc Natl Acad Sci USA 101, 11755-11760.

Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004b). Human microRNA genes are frequently located at fragile sites and genomic regions involved in cancers. Proc Natl Acad Sci USA 101, 2999-3004.

Chen, C. Z., Li, L., Lodish, H. F., and Bartel, D. P. (2004). MicroRNAs modulate hematopoietic lineage differentiation. Science 303, 83-86.

Chen, C. Z., and Lodish, H. F. (2005). MicroRNAs as regulators of mammalian hematopoiesis. Semin Immunol 17, 155-165.

Chou and Roizman, 1992, PNAS 89: 3266-3270

Chou et al., 1994, J. Virol 68: 8304-8311

De Geest, B. R., Van Linthout, S. A., and Collen, D. (2003). Humoral immune response in mice against a circulating antigen induced by adenoviral transfer is strictly dependent on expression in antigen-presenting cells. Blood 101, 2551-2556.

Follenzi, A., Sabatino, G., Lombardo, A., Boccaccio, C., and Naldini, L. (2002). Efficient gene delivery and targeted expression to hepatocytes in vivo by improved lentiviral vectors. Hum Gene Ther 13, 243-260.

Follenzi, A., Battaglia, M., Lombardo, A., Annoni, A., Roncarolo, M. G., and Naldini, L. (2004). Targeting lentiviral vector expression to hepatocytes limits transgene-specific immune response and establishes long-term expression of human antihemophilic factor IX in mice. Blood 103, 3700-3709.

Gentil, M. A., Rocha, J. L., Rodríguez-Algarra, G., Pereira, P., Lopez, R., Bernal, G., Muñoz, J., Naranjo, M., and Mateos, J. (1999) Impaired kidney transplant survival in patients with antibodies to hepatitis C virus. Nephrol Dial Transplant 14, 2455-2460.

Griffiths-Jones, S., Grocock, R. J., van Dongen, S., Bateman, A., and Enright, A. J. (2006). miRBase: microRNA sequences, targets and gene nomenclature. Nucleic Acids Res 34, D140-144.

He, L., and Hannon, G. J. (2004). MicroRNAs: small RNAs with a big role in gene regulation. Nat Rev Genet 5, 522-531.

Houbaviy, H. B., Murray, M. F., and Sharp, P. A. (2003). Embryonic stem cell-specific MicroRNAs. Dev Cell 5, 351-358.

Iorio, M. V., Ferracin, M., Liu, C. G., Veronese, A., Spizzo, R., Sabbioni, S., Magri, E., Pedriali, M., Fabbri, M., Campiglio, M., et al. (2005). MicroRNA gene expression deregulation in human breast cancer. Cancer Res 65, 7065-7070.

Kakimi K, Isogawa M, Chung J, Sette A, Chisari F V. Immunogenicity and tolerogenicity of hepatitis B virus structural and nonstructural proteins: implications for immunotherapy of persistent viral infections. J Virol. 2002; 76:8609-8620

Kasashima, K., Sakota, E., and Kozu, T. (2004). Discrimination of target by siRNA: designing of AML1-MTG8 fusion mRNA-specific siRNA sequences. Biochimie 86, 713-721.

Lagos-Quintana, M., Rauhut, R., Yalcin, A., Meyer, J., Lendeckel, W., and Tuschl, T. (2002). Identification of tissue-specific microRNAs from mouse. Curr Biol 12, 735-739.

Leavitt A D, Robles G, Alesandro N, Varmus H E. (1996) Human immunodeficiency virus type 1 integrase mutants retain in vitro integrase activity yet fail to integrate viral DNA efficiently during infection. J Virol. February; 70(2): 721-8.

Lombardo A, Genovese P, Beausejour C M, Colleoni S, Lee Y L, Kim K A, Ando D, Urnov F D, Galli C, Gregory P D, Holmes M C, Naldini L. (2007) Gene editing in human stem cells using zinc finger nucleases and integrase-defective lentiviral vector delivery. Nat Biotechnol. 25(11):1298-306

Liu Z X, Govindarajan S, Okamoto S, Dennert G. Fas- and tumor necrosis factor receptor 1-dependent but not perforin-dependent pathways cause injury in livers infected with an adenovirus construct in mice. Hepatology. 2000; 31:665-673

Lüth S, Huber S, Schramm C, Buch T, Zander S, Stadelmann C, Brück W, Wraith D C, Herkel J, Lohse A W. (2008) Ectopic expression of neural autoantigen in mouse liver suppresses experimental autoimmune neuroinflammation by inducing antigen-specific Tregs. J Clin Invest. 118(10): 3403-3410.

Mansfield, J. H., Harfe, B. D., Nissen, R., Obenauer, J., Srineel, J., Chaudhuri, A., Farzan-Kashani, R., Zuker, M., Pasquinelli, A. E., Ruvkun, G., et al. (2004). MicroRNA-responsive 'sensor' transgenes uncover Hox-like and other developmentally regulated patterns of vertebrate microRNA expression. Nat Genet 36, 1079-1083.

Marodon G, Fisson S, Levacher B, Fabre M, Salomon B L, Klatzmann D. (2006) Induction of antigen-specific tolerance by intrathymic injection of lentiviral vectors. Blood. 108(9):2972-8.

MacLean et al., 1991, J Gen Virol 72: 632-639

Michael M et al, Mol Can Res (2003) 1:882-891

Mingozzi, F., Liu, Y. L., Dobrzynski, E., Kaufhold, A., Liu, J. H., Wang, Y., Arruda, V. R., High, K. A., and Herzog, R. W. (2003). Induction of immune tolerance to coagulation factor IX antigen by in vivo hepatic gene transfer. J Clin Invest 111, 1347-1356.

Miyahira Y, Murata K, Rodriguez D, Rodriguez J R, Esteban M, Rodrigues M M, Zavala F. (1995) Quantification of antigen specific CD8+ T cells using an ELISPOT assay. J Immunol Methods. April 12; 181(1):45-54.

Naldini L, Blomer U, Gage F H, Trono D, Verma I M. (1996) Efficient transfer, integration, and sustained long-term expression of the transgene in adult rat brains injected with a lentiviral vector. Proc Natl Acad Sci USA. 93(21): 11382-8.

Nightingale S J, Hollis R P, Pepper K A, Petersen D, Yu X J, Yang C, Bahner I, Kohn D B. (2006) Transient gene expression by nonintegrating lentiviral vectors. Mol Ther. June; 13(6):1121-32. Epub 2006 Mar. 23.

Philippe S, Sarkis C, Barkats M, Mammeri H, Ladroue C, Petit C, Mallet J, Serguera C. (2006) Lentiviral vectors with a defective integrase allow efficient and sustained transgene expression in vitro and in vivo. Proc Natl Acad Sci USA. 103(47):17684-9.

Rice and Knipe, 1990, J. Virol 64: 1704-1715

Sempere, L. F., Freemantle, S., Pitha-Rowe, I., Moss, E., Dmitrovsky, E., and Ambros, V. (2004). Expression profiling of mammalian microRNAs uncovers a subset of brain-expressed microRNAs with possible roles in murine and human neuronal differentiation. Genome Biol 5, R13.

Smith et al., 1992, Virology 186: 74-86

Thomas, C. E., Ehrhardt, A., and Kay, M. A. (2003). Progress and problems with the use of viral vectors for gene therapy. Nat Rev Genet 4, 346-358.

Vargas J Jr, Gusella G L, Najfeld V, Klotman M E, Cara A. (2004) Novel integrase-defective lentiviral episomal vectors for gene transfer. Hum Gene Ther. 15(4):361-72.

Toniutto, P., Fabris, C., Bitetto, D., Fornasiere, E., Fumolo, E., Rapetti, R., and Pirisi, M. (2008) Antiviral treatment in patients with hepatitis C virus-related cirrhosis awaiting liver transplantation. Ther Clin Risk Manag 4, 599-603.

Vargas, J Jr, Gusella G L, Najfeld V, Klotman M E, Cara A (2004). Novel integrase-defective lentiviral episomal vectors for gene transfer. Hum. Gene Ther. 2004 April; 15(4):361-72

Verma, I. M., and Weitzman, M. D. (2005). GENE THERAPY: Twenty-First Century Medicine. Annu Rev Biochem 74, 711-738.

Yáñez-Muñoz R J, Balaggan K S, MacNeil A, Howe S J, Schmidt M, Smith A J, Buch P, MacLaren R E, Anderson P N, Barker S E, Duran Y, Bartholomae C, von Kalle C, Heckenlively J R, Kinnon C, Ali R R, Thrasher A J.

(2006) Effective gene therapy with nonintegrating lentiviral vectors. Nat Med. 12(3):348-53

The invention claimed is:

1. A gene vector adapted for transient expression of a transgene in a liver cell comprising a regulatory sequence operably linked to the transgene, wherein the regulatory sequence prevents or reduces expression of said transgene in hematopoietic lineage antigen presenting cells, wherein the transgene is operably linked to a hepato-specific promoter, wherein the vector is an integration defective lentiviral vector (IDLV), and wherein the regulatory sequence comprises one or more target sequences each of which is independently selected from sequences targeted by miR-142, miR-155, miR-223 or miR-181.

2. The vector according to claim 1, wherein the IDLV vector is derived from HIV.

3. The vector according to claim 1, wherein the target sequence is a sequence targeted by miR-142.

4. The vector according to claim 3, wherein the regulatory sequence comprises four copies of a miR-142 target sequence.

5. The vector according to claim 1, wherein at least one or more of the target sequences is fully or partially complementary to the miR-142, miR-155, miR-223 or miR-181 sequence.

6. The vector according to claim 1, wherein the transgene product is a therapeutic protein.

7. The vector according to claim 1, wherein the trans gene product is an antigen.

8. The vector according to claim 7, wherein the antigen is selected from the group consisting of an endogenous antigen, an exogenous antigen, an alloantigen and an autoantigen.

9. The vector according to claim 8, wherein the antigen is an exogenous antigen.

10. The vector according to claim 1, wherein the hepato-specific promoter is a promoter selected from the group of albumin promoter, trans-thyretin promoter, alpha1-antitrypsin promoter, synthetic apoE/alpha1-antitrypsin promoter and synthetic ET promoter.

11. The vector according to claim 1, wherein the vector is in the form of a viral vector particle.

12. A set of DNA constructs for producing the vector particle of claim 11 comprising a packagable vector genome, gag, pol and env or functional substitutes thereof.

13. The set of DNA constructs according to claim 12, wherein said constructs encode a defective integrase.

14. The set of DNA constructs according to claim 12, wherein said constructs comprise altered LTR sites and wherein the altered LTR sites prevent integration of the lentiviral vector genome.

15. A pharmaceutical composition comprising the vector of claim 1.

16. An isolated cell infected or transduced with the vector of claim 1.

17. The vector according to claim 1 for use in inducing or enhancing immunological tolerance against an antigen in a subject.

18. The vector according to claim 1, wherein the antigen is an exogenous antigen administered as part of a protein replacement therapy.

19. The vector according to claim 1, wherein at least one or more of the target sequence has perfect complementarity to the miR-142, miR-155, miR-223 or miR-181 sequence.

20. The vector according to claim 19, wherein the vector includes more than one copy of an miRNA target sequence.

21. A pharmaceutical composition comprising the viral vector particle of claim 11.

22. An isolated cell infected or transduced with the viral vector particle of claim 11.

23. The viral vector particle according to claim 11, for use in inducing or enhancing immunological tolerance against an antigen in a subject.

24. The viral vector particle according to claim 11, wherein the transgene product is an antigen, and wherein the antigen is an exogenous antigen administered as part of a protein replacement therapy.

* * * * *